US012594082B2

(12) United States Patent
Sidebotham et al.

(10) Patent No.: US 12,594,082 B2
(45) Date of Patent: Apr. 7, 2026

(54) SURGICAL CUTTING TOOL

(71) Applicant: LRS Science and Technology, LLC, Mendham, NJ (US)

(72) Inventors: Christopher G. Sidebotham, Mendham, NJ (US); Leon Roitburg, East Hanover, NJ (US); Randall J. Lewis, Bethesda, MD (US)

(73) Assignee: LRS Science and Technology, LLC, Mendham, NJ (US)

( * ) Notice: Subject to any disclaimer, the term of this patent is extended or adjusted under 35 U.S.C. 154(b) by 223 days.

(21) Appl. No.: 18/302,295

(22) Filed: Apr. 18, 2023

(65) Prior Publication Data

US 2023/0255648 A1    Aug. 17, 2023

Related U.S. Application Data

(63) Continuation of application No. PCT/US2021/054429, filed on Oct. 11, 2021.

(60) Provisional application No. 63/093,717, filed on Oct. 19, 2020.

(51) Int. Cl.
*A61B 17/16* (2006.01)
*A61B 17/00* (2006.01)

(52) U.S. Cl.
CPC ...... *A61B 17/1666* (2013.01); *A61B 2017/00526* (2013.01)

(58) Field of Classification Search
CPC .................................................. A61B 17/1666
See application file for complete search history.

(56) References Cited

U.S. PATENT DOCUMENTS

| | | | |
|---|---|---|---|
| 8,679,124 | B2 | 3/2014 | Lechot et al. |
| 9,101,368 | B2 | 8/2015 | Sidebotham et al. |
| 10,499,931 | B2 | 12/2019 | Xie et al. |
| 2010/0145342 | A1 | 6/2010 | Grace et al. |

(Continued)

FOREIGN PATENT DOCUMENTS

| | | |
|---|---|---|
| CN | 106859726 A | 6/2017 |
| CN | 108472046 A | 8/2018 |

(Continued)

OTHER PUBLICATIONS

International Search Report and Written Opinion mailed in International Application No. PCT/US2021/054429 on Mar. 11, 2022, by the European Searching Authority (16 pages).

(Continued)

*Primary Examiner* — Andrew Yang
(74) *Attorney, Agent, or Firm* — Klarquist Sparkman, LLP

(57) ABSTRACT

A hemispherical cutting tool has a frame having a first end portion and a second end portion. Curved side panels are coupled to the frame and arranged about the rotational axis of the cutting tool, and have cutting teeth and engagement members extending inwardly into the frame from edge portions of the curved side panels in a direction toward a hollow interior of the hemispherical cutting tool. A dome panel is coupled to the second end portion of the frame such that the cutting tool has a hemispherical shape, the dome panel comprising cutting teeth and a plurality of engagement members extending inwardly into the frame in a direction toward the hollow interior of the tool. The frame is injection molded around the curved side panels and the dome panel such that the engagement members of the curved side panels and the dome panel are embedded in the frame.

24 Claims, 31 Drawing Sheets

(56) References Cited

U.S. PATENT DOCUMENTS

| | | |
|---|---|---|
| 2018/0098776 A1 | 4/2018 | Sidebotham et al. |
| 2018/0360476 A1 | 12/2018 | Fortin et al. |

FOREIGN PATENT DOCUMENTS

| | | | |
|---|---|---|---|
| EP | 2957245 | A1 | 12/2015 |
| JP | 2013248877 | A | 12/2013 |
| JP | 2015506238 | A | 3/2015 |
| WO | 2017077340 | A1 | 5/2017 |

OTHER PUBLICATIONS

English translation of Office Action issued by the Japan Patent Office on Apr. 15, 2025, in corresponding Application No. JP 2023-548172, 4 pages.

AXIAL FORCE
APPLIED BY
SURGEON

TORSIONAL FORCE
APPLIED BY
POWER TOOL

ACETABULAR IMPLANT

PRESS FIT ACETABULAR IMPLANT AS PART OF A TOTAL HIP PROCEDURE

PREPARATION OF THE ACETABULUM

ACETABULAR REAMER
HOLLOW SPHERICAL CUTTER

BONE CHIP
OPENING

RADIAL CUTTING EDGE
MATCHES
SPHERICAL REAMER

FUNNEL ANGLE
FOR BONE DEBRIS

TOOTH HEIGHT
ANGLE (β)

FUNNEL
ANGLE

TOOTH HEIGHT

CUTTING
EDGE
RADIUS

CUTTING TOOTH
GEOMETRY SHOWN

CUTTING TOOTH HEIGHT SET

CUTTING TEETH ZONES BASED ON FUNCTION

ACETABULAR REAMER

TRANSITIONAL TEETH

EQUATORIAL TEETH

POLAR TEETH

ACETABULUM UNDERSIZED TO REAMER BY ONE (1)mm

REAMER INTRODUCED 100% TEETH ARE PRIMARILY END CUTTING

REAMER INTRODUCED APPROXIMATELY 50% TEETH ARE TRANSITIONING FROM SIDE CUTTING TO END CUTTING

INITIATION OF REAMING TEETH ARE PRIMARILY SIDE CUTTING

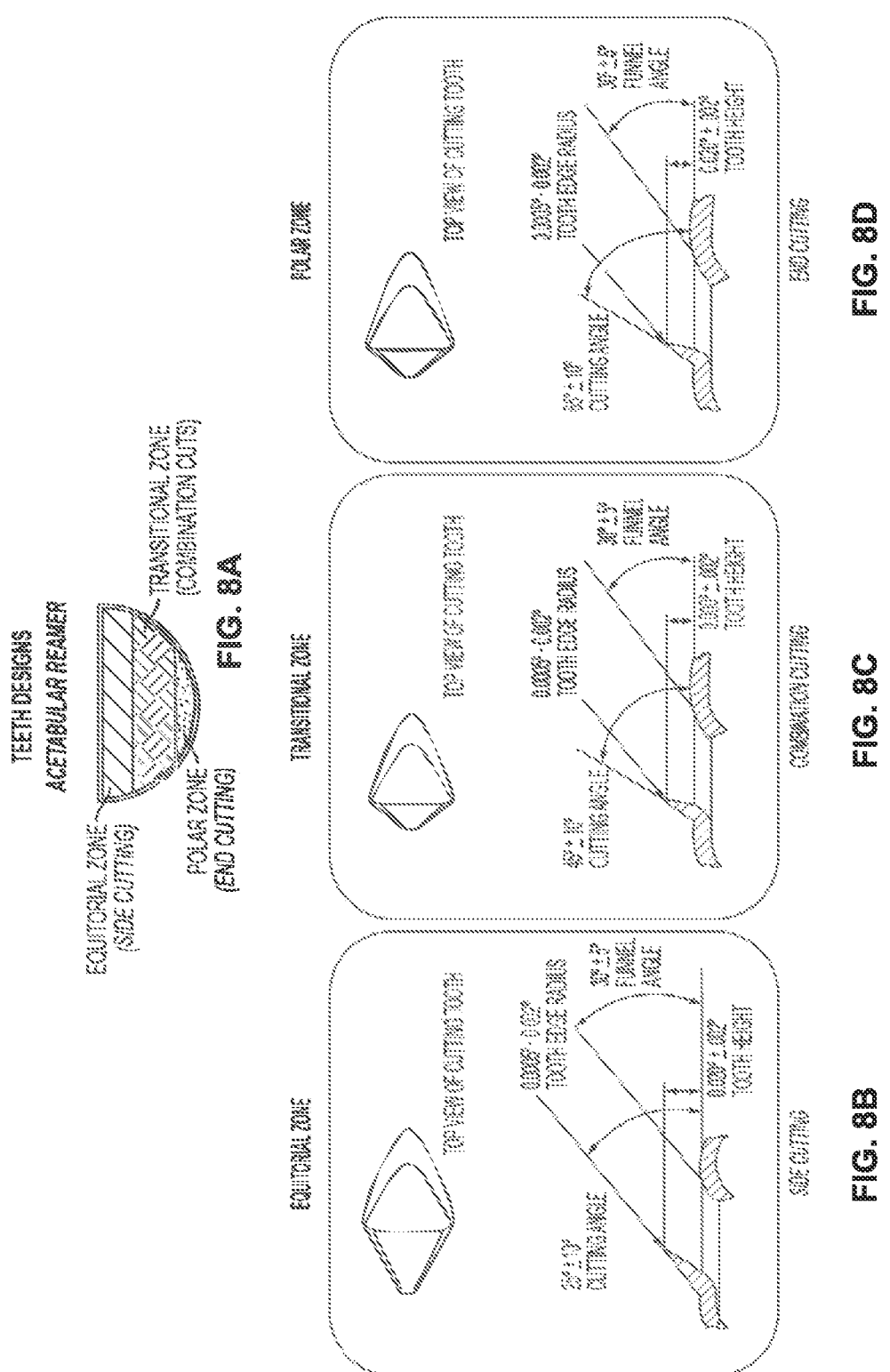

CUTTING BONE
*FRICTION-HEAT ASSOCIATED WITH BONE CHIP*

$F_c = -2m\Omega (v)$ WHERE, m = MASS OF THE REAMER
$\Omega$ = ANGULAR VELOCITY VECTOR
v = VELOCITY OF ROTATING SYSTEM

STAMPED CUTTING
PANELS

INJECTION MOLDING TOOL
CREATES PLASTIC FRAME
AROUND PANELS

FINISHED REAMER IS STRUCTURALLY
SOUND THROUGH THE FRAME AND
MAINTAINS CUTTER SPHERICITY AND
TOLERANCES WITHIN .004"

Hollow Spherical Reamers:

*Acetabulum Preparation*

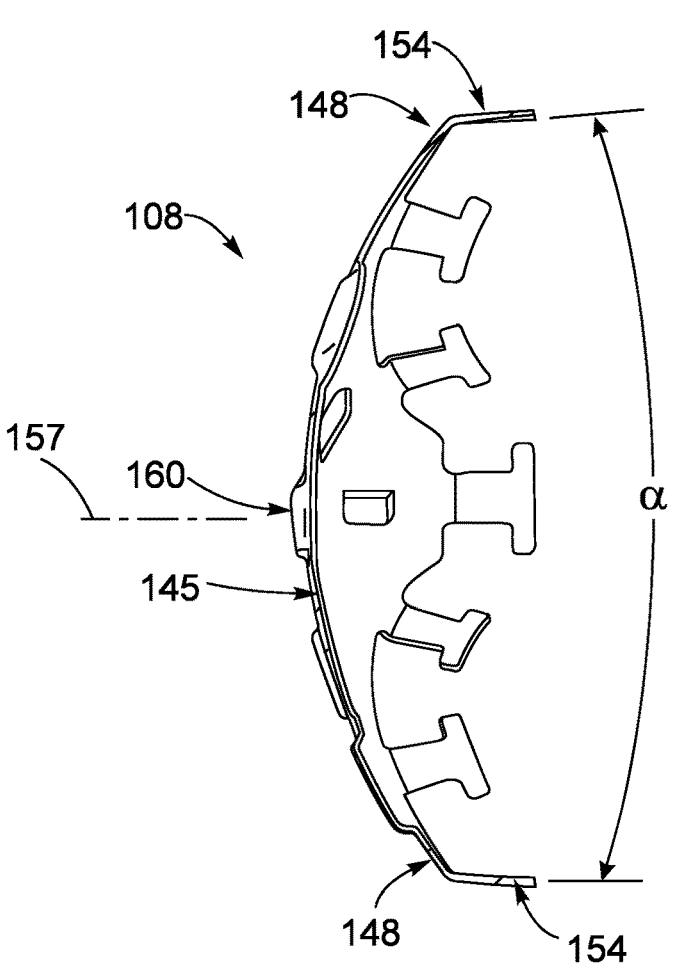
FIG. 21C
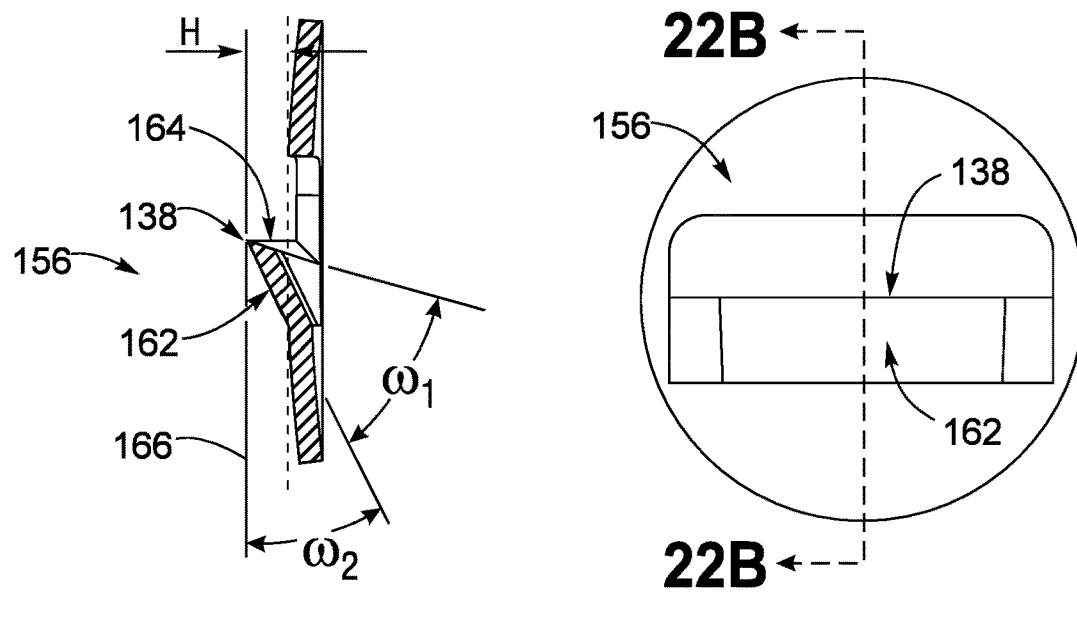
FIG. 22B          FIG. 22A

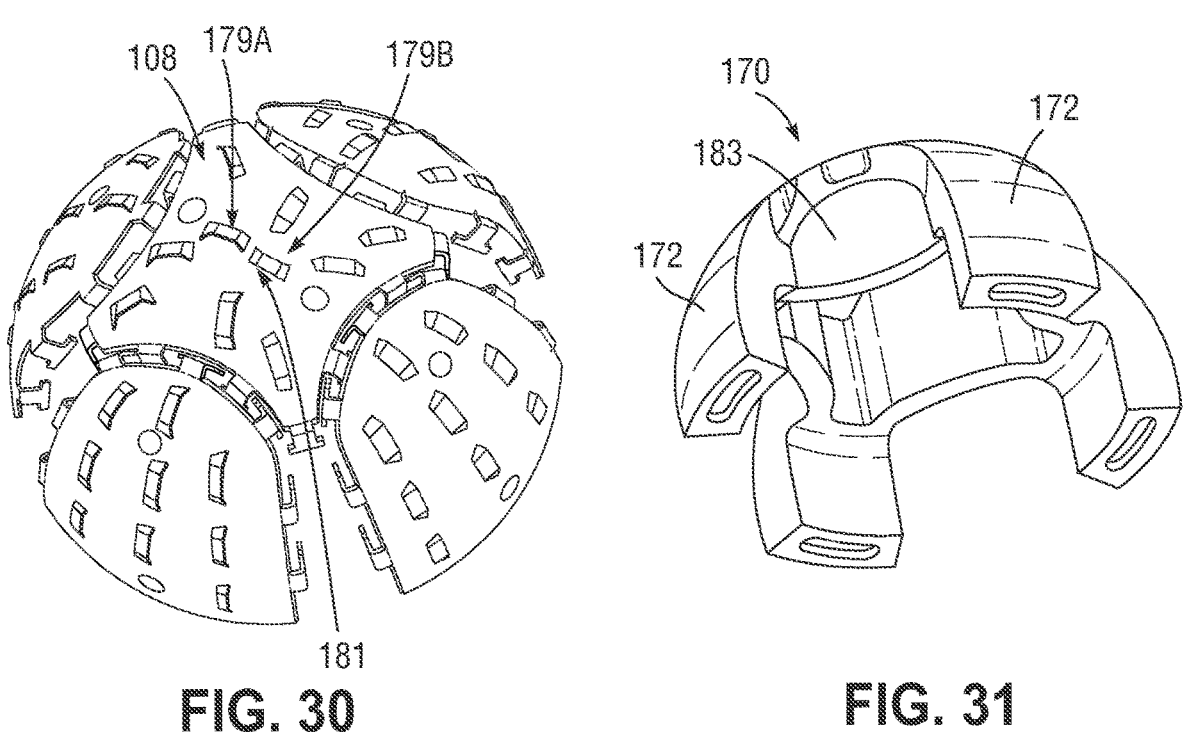
FIG. 30
FIG. 31
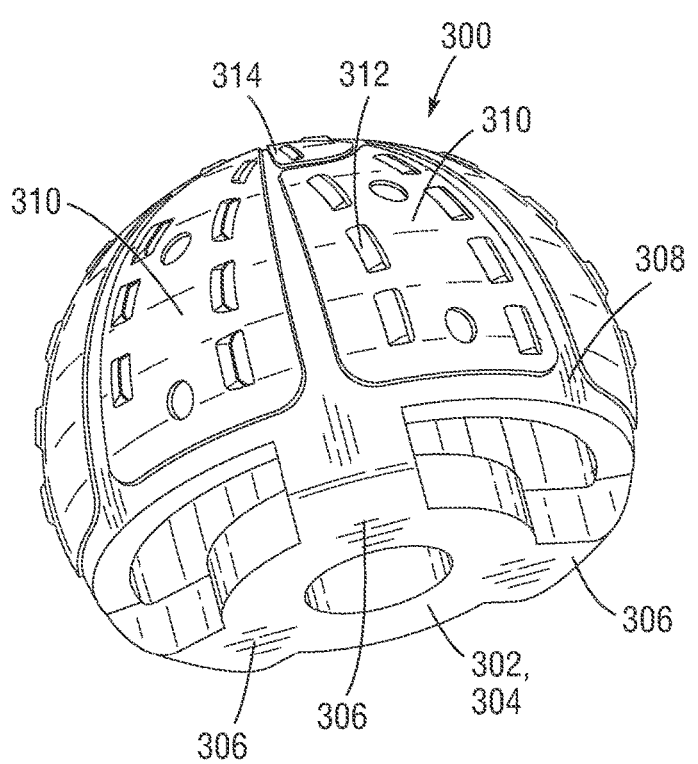
FIG. 32

SURGICAL CUTTING TOOL

CROSS REFERENCE TO RELATED APPLICATIONS

The present application is a continuation of International Patent Application No. PCT/US2021/054429, filed on Oct. 11, 2021, which application claims the benefit of U.S. Provisional Application No. 63/093,717, filed on Oct. 19, 2020. Each of the above-referenced applications is incorporated herein by reference in its entirety.

FIELD

This disclosure pertains to surgical cutting tool systems and associated methods relating to orthopedic surgery, and more specifically, preparation of prosthetic hip implantations.

BACKGROUND

Cutting tools, such as medical reamers used by surgeons, generally have a cutting surface that is able to cut and/or remove material from an object. For example, in many different disciplines in orthopedics cutting tools are used for machining bone in the preparation of artificial joints including hips, knees, elbows and shoulders, and also in the repair of long bone fractures. For example, spherical or hemispherical reamers can be used to shape the acetabulum in total hip replacement procedures. The design and method of manufacturing cutting surfaces of such cutting tools can affect the efficiency, functional life of the spherical reamer and cost in manufacturing. Accordingly, there exists a need for improvements relating to design and manufacturing of surgical cutting tools.

SUMMARY

Disclosed herein are exemplary embodiments of devices, systems, and related methods for performing orthopedic surgery. In some implementations, the devices and systems can be used in preparing a prosthetic hip implantation. In some embodiments, the devices and systems can be included in a sterile kit. In some embodiments, some of the devices can be disposable.

In some embodiments, improved cutting tools and methods of manufacturing the same are provided.

In certain implementations, the cutting tools can comprise medical reamers, including hemispherical or acetabular reamers, along with the design of different cutting teeth in specific zones of the reamers and the improved method of making these reamers and their cutting edges.

In a representative embodiment, a hemispherical cutting tool comprises a frame having a first end portion and a second end portion, and defining an axis of rotation of the hemispherical cutting tool. The cutting tool further comprises a plurality of curved side panels coupled to the frame and arranged about the axis of rotation of the cutting tool, the curved side panels comprising a plurality of cutting teeth and a plurality of engagement members extending inwardly into the frame from edge portions of the curved side panels in a direction toward a hollow interior of the hemispherical cutting tool. The frame further comprises a dome panel coupled to the second end portion of the frame such that the cutting tool has a hemispherical shape, the dome panel comprising a plurality of cutting teeth and a plurality of engagement members extending inwardly from edge portions of the dome panel into the frame in a direction toward the hollow interior of the hemispherical cutting tool. The frame is injection molded around the curved side panels and the dome panel such that the engagement members of the curved side panels and the dome panel are embedded in the injection molded frame.

In any or all of the disclosed embodiments, side edge portions and distal edge portions of the curved side panels comprise engagement members.

In any or all of the disclosed embodiments, the engagement members of the curved side panels comprise T-shaped members.

In any or all of the disclosed embodiments, the frame comprises a first polymeric frame member comprising an annular body, and a second polymeric frame member comprising a plurality of curved extension members coupled to the annular body of the first polymeric frame member.

In any or all of the disclosed embodiments, one of the first or second polymeric frame members comprises a plurality of coupling portions configured to be received in openings defined in the other of the first or second polymeric frame members.

In any or all of the disclosed embodiments, the cutting teeth of the curved side panels are arranged in columns, and cutting edges of the cutting teeth are longitudinally offset from each other in adjacent columns and at least partially overlap with each other in the circumferential direction.

In any or all of the disclosed embodiments, the cutting teeth of the curved side panels are arranged in columns, the cutting teeth of a central column of cutting teeth of each curved side panel are aligned with a central axis of the curved side panel, and cutting teeth of columns of cutting teeth that are circumferentially offset from the central column of cutting teeth are angled toward the central column of cutting teeth.

In any or all of the disclosed embodiments, the cutting teeth of the curved side panels comprise a long dimension and a short dimension, and the long dimensions of the cutting teeth are oriented longitudinally on a hemispherical surface of the cutting tool.

In any or all of the disclosed embodiments, the axis of rotation of the hemispherical cutting tool intersects a cutting tooth of the plurality of cutting teeth of the dome panel.

In any or all of the disclosed embodiments, the dome panel comprises a plurality of lobes separated by concave edge portions, each of the lobes comprising an engagement member.

In another representative embodiment, a hemispherical cutting tool comprises a polymeric frame comprising a first polymeric frame member coupled to a second polymeric frame member and defining an axis of rotation of the hemispherical cutting tool, the first polymeric frame member comprising an annular body and defining a first end portion of the frame, the second polymeric frame member comprising a plurality of curved extension members coupled to the annular body of the first polymeric frame member and converging toward a second end portion of the polymeric frame. A metal dome panel is coupled to the second polymeric frame member at the second end portion of the polymeric frame, the metal dome panel comprising a plurality of cutting teeth, and a plurality of curved metal side panels are coupled to the polymeric frame and arranged about the axis of rotation of the hemispherical cutting tool.

In any or all of the disclosed embodiments, the curved metal side panels comprise a plurality of engagement members extending inwardly from edge portions of the curved metal side panels into the second polymeric frame member in a direction toward a hollow interior of the hemispherical cutting tool.

In any or all of the disclosed embodiments, side edge portions and distal edge portions of the curved metal side panels comprise engagement members.

In any or all of the disclosed embodiments, the metal dome panel comprises a plurality of engagement members extending from edge portions of the metal dome panel inwardly into the second polymeric frame member in a direction toward the hollow interior of the hemispherical cutting tool.

In any or all of the disclosed embodiments, the engagement members of the curved metal side panels comprise T-shaped members.

In any or all of the disclosed embodiments, the frame is injection molded around the curved metal side panels and the metal dome panel such that the engagement members of the curved metal side panels and the metal dome panel are embedded in the injection molded frame.

In any or all of the disclosed embodiments, one of the first or second polymeric frame members comprises a plurality of coupling portions configured to be received in openings defined in the other of the first or second polymeric frame members.

In any or all of the disclosed embodiments, the cutting teeth of the curved metal side panels comprise a long dimension and a short dimension, and the long dimensions of the cutting teeth are oriented longitudinally on a hemispherical surface of the cutting tool.

In any or all of the disclosed embodiments, the axis of rotation of the hemispherical cutting tool intersects a cutting tooth of the plurality of cutting teeth of the metal dome panel.

In any or all of the disclosed embodiments, the metal dome panel comprises a plurality of lobes separated by concave edge portions, each of the lobes comprising an engagement member.

In another representative embodiment, a hemispherical cutting tool comprises a frame comprising a first polymeric frame member coupled to a second polymeric frame member and defining an axis of rotation of the hemispherical cutting tool, the first polymeric frame member comprising an annular body and defining a first end portion of the frame, the second polymeric frame member comprising a plurality of curved extension members coupled to the annular body of the first polymeric frame member and converging toward a second end portion of the polymeric frame. A plurality of curved side panels is coupled to the frame and arranged about the axis of rotation of the cutting tool, the curved side panels comprising a plurality of cutting teeth and a plurality of engagement members extending inwardly into the frame from edge portions of the curved side panels in a direction toward a hollow interior of the hemispherical cutting tool. A dome panel is coupled to the second end portion of the frame such that the cutting tool has a hemispherical shape, the dome panel comprising a plurality of cutting teeth and a plurality of engagement members extending inwardly from edge portions of the dome panel into the frame in a direction toward the hollow interior of the hemispherical cutting tool, and the second polymeric frame member is injection molded around the curved side panels and the dome panel such that the engagement members of the curved side panels and the dome panel are embedded in the second polymeric frame member.

In another representative embodiment, a method of making the hemispherical cutting tool of any of the embodiments described herein comprises situating the dome panel and the plurality of side panels in a mold, and injecting a polymeric material into the mold to form at least a portion of the frame.

In another representative embodiment, a method comprises cutting bone with the hemispherical cutting tool of any of the embodiments described herein.

In another representative embodiment, a cutting tool is provided with a cutting surface on a first side of the cutting tool and an attachment member on a second side of the cutting tool. The cutting surface can include a plurality of cutting edges and the attachment member can be configured to be coupled to a powered driving member (e.g., a drill). The cutting tool can comprise an axis of rotation and the cutting surface can define a plurality of latitude lines. The plurality of cutting edges can be oriented at varying orientation angles relative to the latitude lines.

In any or all of the disclosed embodiments, the plurality of cutting edges can be increased to three or more different zones and respective cutting edges in the different zones have different characteristics. The different zones can comprise a polar zone, a transition zone, and an equatorial zone. Respective cutting edges can define a cutting angle between the cutting edge and a first side of the cutting tool, and the cutting angle between cutting edges in the polar zone can be larger than those defined by cutting edges in the transition zone, and the cutting angle between cutting edges in the transition zone can be larger than those defined by cutting edges in the equatorial zone. In some implementations, the tooth height can be the same (i.e., substantially the same) regardless of the cutting angle.

In any or all of the disclosed embodiments, the orientation angles can vary depending on whether the respective cutting edges are in the polar zone, the transition zone, or the equatorial zone, and the orientation angle of respective cutting edges in the equatorial zone is greater than the orientation angle of respective cutting edges in the transition zone, and the orientation angle of respective cutting edges in the transition zone is greater than the orientation angle of respective cutting edges in the polar zone.

In any or all of the disclosed embodiments, the thickness of the side wall can be less than 0.040 inches, or in some cases, between 0.022 inches and 0.040 inches. Openings can be provided adjacent respective cutting edges, the respective openings defining a funnel angle that is between 20 and 40 degrees. In some cases, the funnel angle can be between 25 and 35 degrees.

In any or all of the disclosed embodiments, the cutting surface can be a panel and the cutting tool can comprise a plurality of separate panels. The cutting tool can include a frame member and the plurality of separate panels can be coupled to the frame member.

In another representative embodiments, a method for forming a cutting tool is provided. The method can include forming a plurality of panels from one or more flat sheets of metal and coupling the plurality of panels to a frame member to form the cutting tool. The plurality of panels can be formed with a plurality of cutting edges and a plurality of openings adjacent respective cutting edges. When coupled to the frame member, the plurality of panels can define a plurality of latitude lines about the axis of rotation of the cutting tool and the plurality of formed cutting edges have orientation angles relative to the latitude lines that vary. In some cases, respective panels can have cutting edges with orientation angles that vary along the respective panel.

In any or all of the disclosed embodiments, the act of forming a plurality of panels can comprise stamping the one or more flat sheets of metal to form a plurality of cavities and punching holes at or adjacent to the plurality of cavity to provide bone-chip-receiving openings. The act of forming the plurality of cavities can include forming a plurality of "V"-shaped cavities.

In any or all of the disclosed embodiments, the act of forming the plurality of panels can include stamping the one or more panels to create a desired height of the cutting edges and to provide a desired curvature of the one or more panels.

In any or all of the disclosed embodiments, the act of coupling the plurality of panels to the frame member can include forming a frame member that comprises a base, and a form dome, and securing the plurality of panels to the frame member and the form dome. In some cases, the act of securing the plurality of panels to the frame member and the form dome can be performed by laser welding or other types of welding. The act of coupling the plurality of panels to the frame member can also include placing the plurality of panels into an injection molding tool and injection molding the frame member around the plurality of panels to create the frame member.

In any or all of the disclosed embodiments, the act of forming a plurality of panels from one or more flat sheets of metal can include forming the plurality of cutting edges with different zones that have cutting edges with different characteristics, the different zones comprising a polar zone, a transition zone, and an equatorial zone. Respective cutting edges can define a cutting angle between the cutting edge and a first side of the cutting tool, and the cutting angle between cutting edges in the polar zone can be larger than those defined by cutting edges in the transition zone, and the cutting angle between cutting edges in the transition zone can be larger than those defined by cutting edges in the equatorial zone.

In any or all of the disclosed embodiments, the act of punching holes at or adjacent to the plurality of cavity can comprise forming bone-chip-receiving openings with a funnel angle that is between 20 and 40 degrees. In addition, in some cases, the one or more flat sheets of metal can have a thickness less than 0.040 inches (1.02 mm).

In any or all of the disclosed embodiments, the method can include determining an effective functional life of the cutting tool.

In another representative embodiment, a cutting tool is provided that can have a cutting surface on a first side of the cutting tool, the cutting surface comprising a plurality of cutting edges, and an attachment member on a second side of the cutting tool, the attachment member being configured to be coupled to a powered driving member. A plurality of cutting edges can be provided in different zones and respective cutting edges in the different zones can have different characteristics.

The foregoing and other objects, features, and advantages of the disclosed technology will become more apparent from the following detailed description, which proceeds with reference to the accompanying figures.

BRIEF DESCRIPTION OF THE DRAWINGS

FIG. 8A illustrates a schematic view of cutting teeth zones and their general functions. FIG. 8B illustrates the cutting teeth of the equatorial zone. FIG. 8C illustrates the cutting teeth of the transitional zone. FIG. 8D illustrates the cutting teeth of the polar zone.

FIGS. 21A-21C are perspective, top plan, and side elevation views, respectively, of a dome panel, according to one embodiment.

US 12,594,082 B2

Figure 21A:
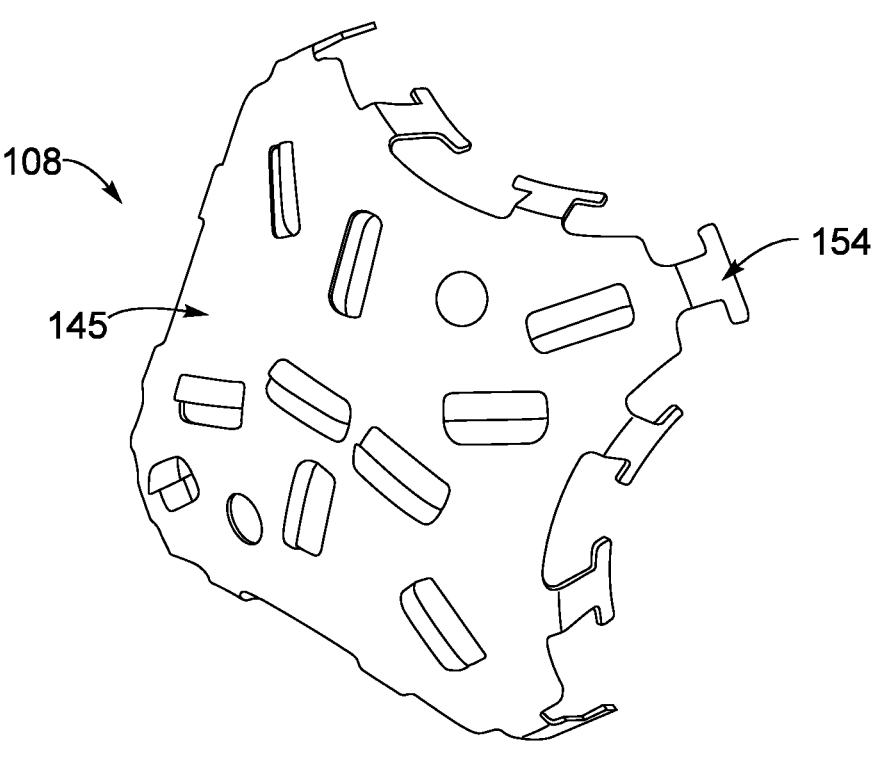
Figure 21B:
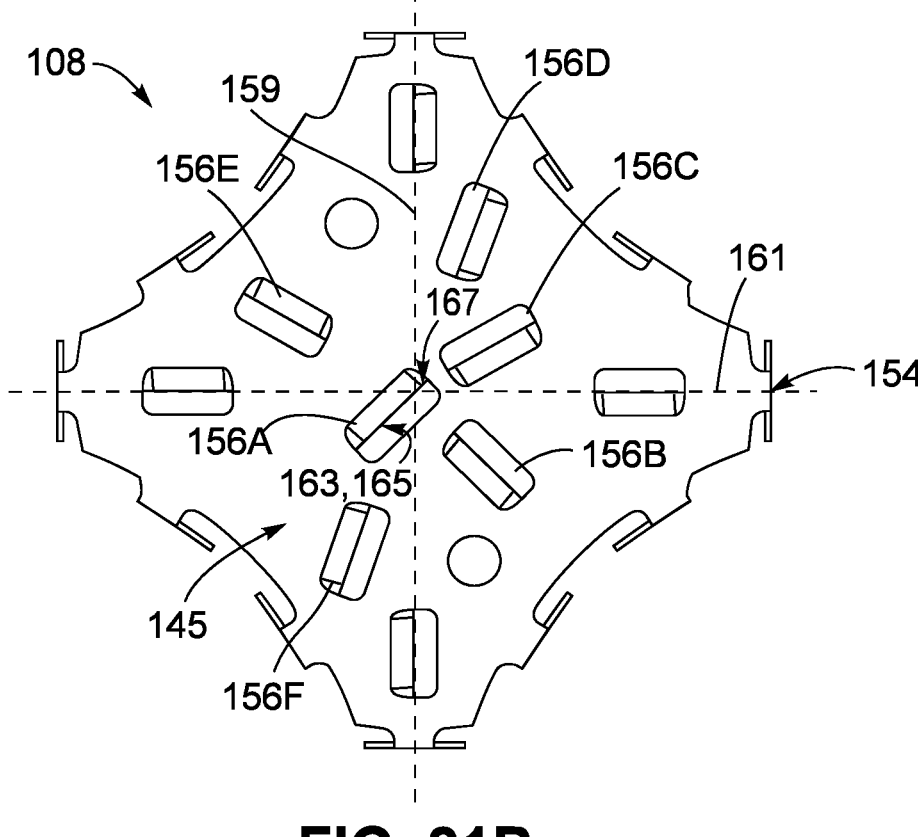

FIG. 22A is a magnified view of a representative cutting tooth of the dome panel of FIGS. 21A-21C.

FIG. 22B is a cross-sectional view of the cutting tooth taken along line 22B-22B of FIG. 22A.

Figures 15A, 15B:
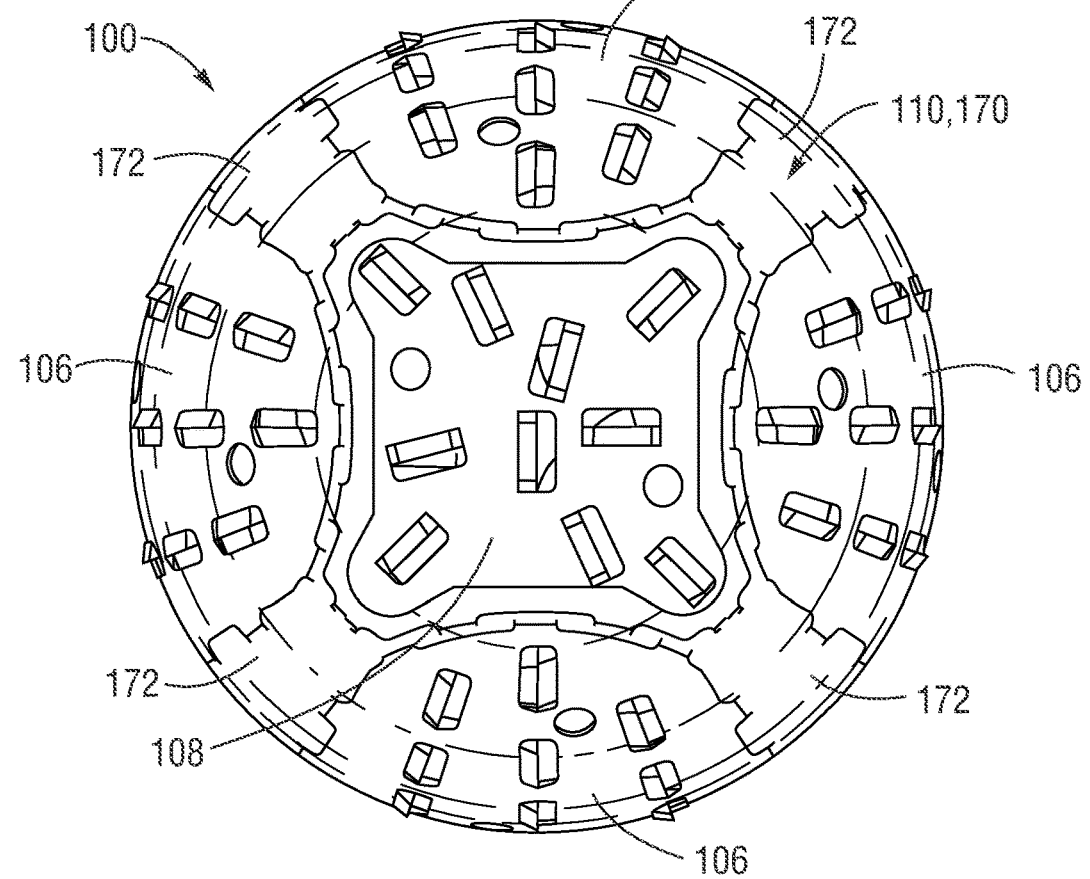
FIGS. 15A-15D are side, top, bottom plan views, and a perspective view, respectively, of a hemispherical cutting tool, according to another embodiment.
Figure 15C:
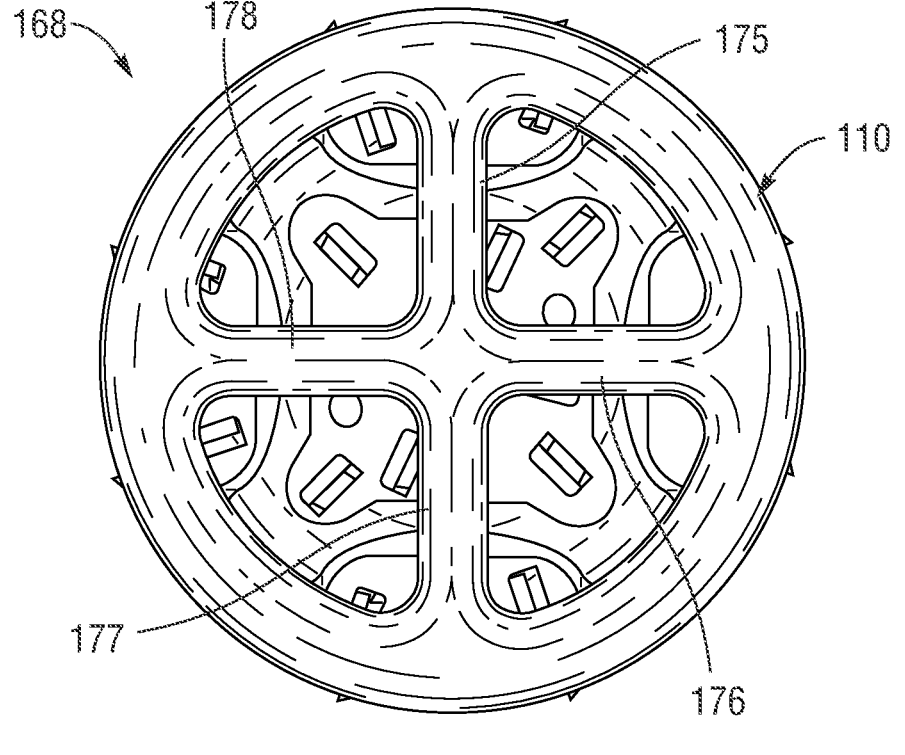
Figure 15D:
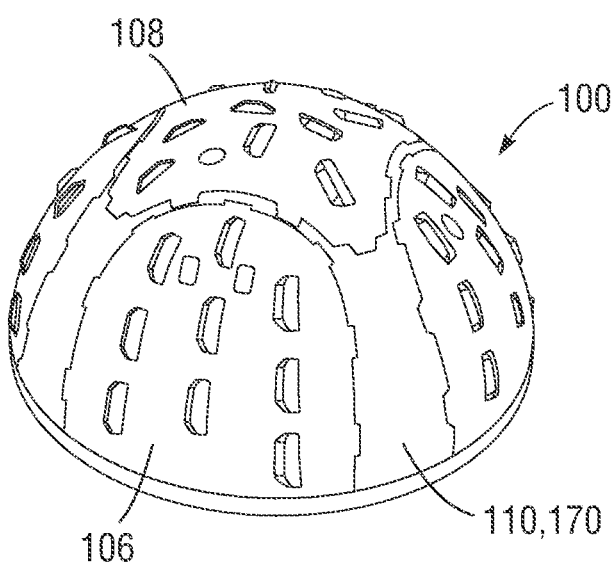
Figure 15E:
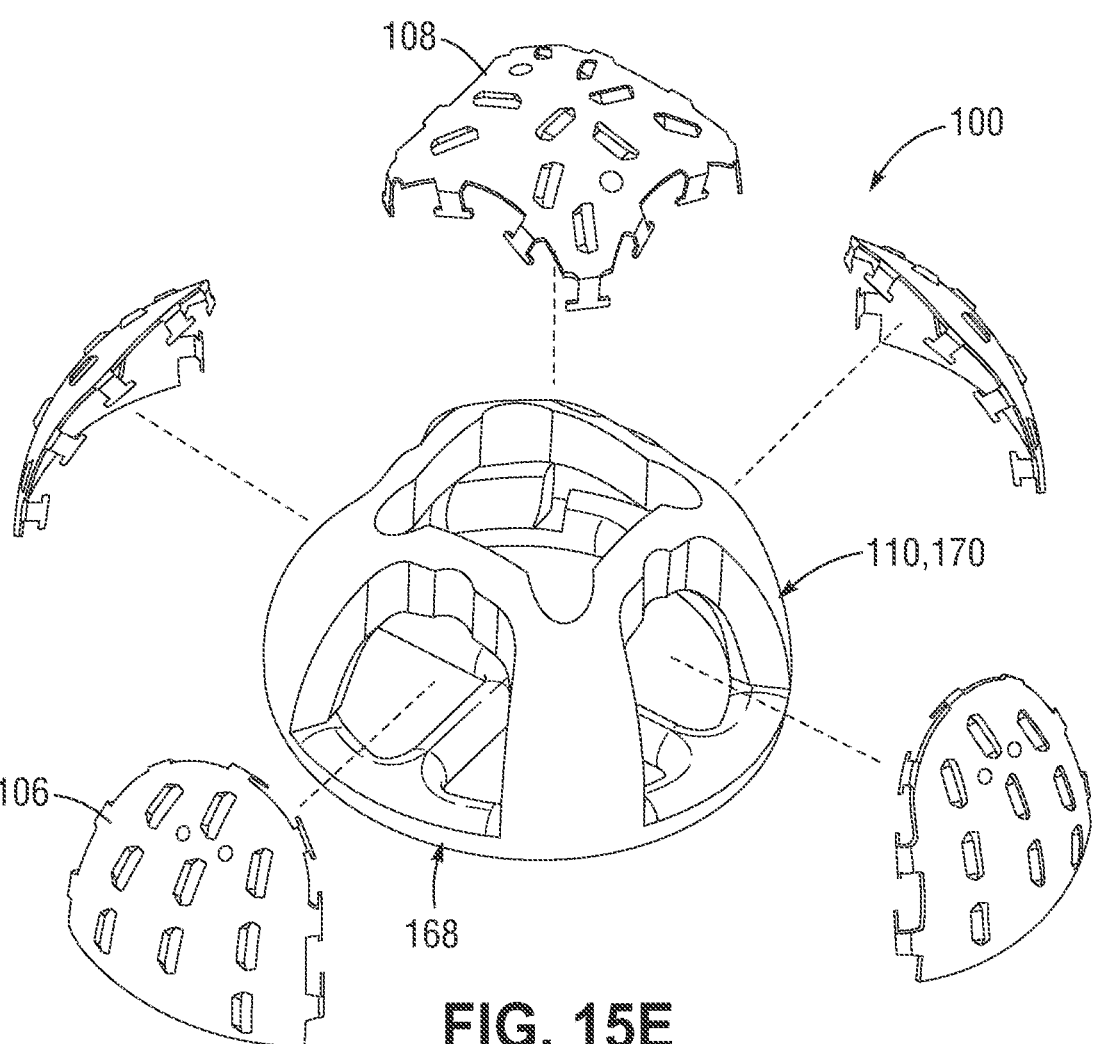
FIG. 15E is an exploded view of the hemispherical cutting tool of FIGS. 15A-15D.
Figure 23:
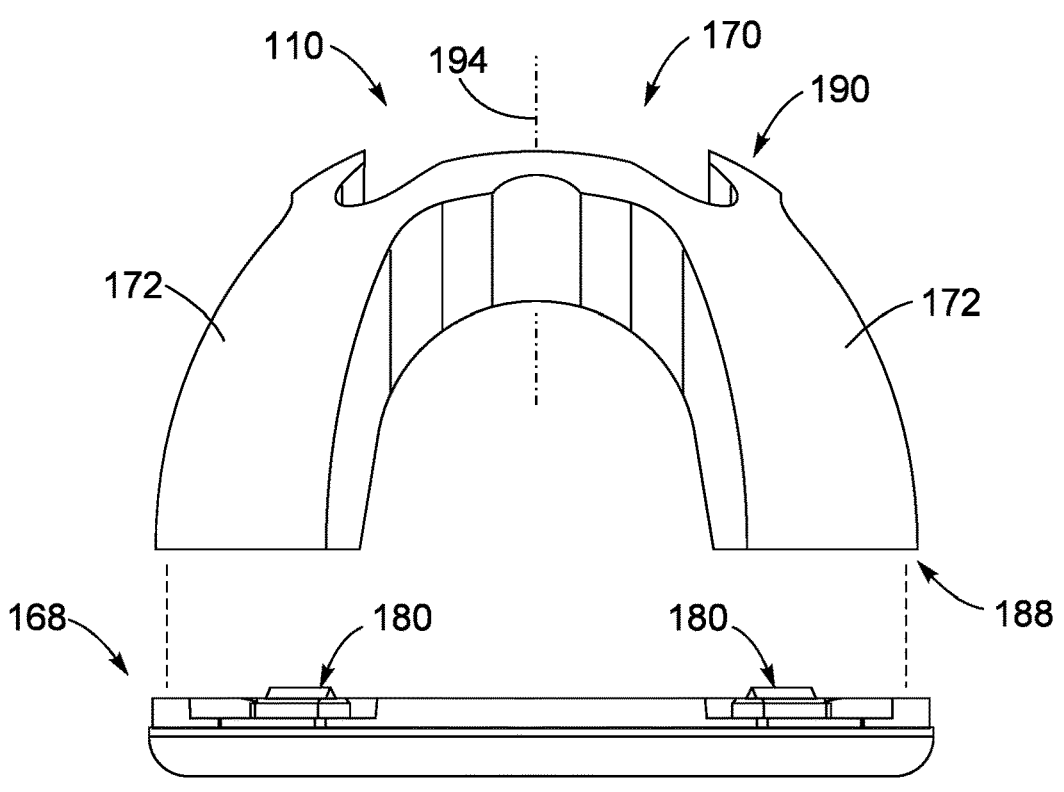

FIG. 23 is an exploded view of a frame member of the hemispherical reamer of FIG. 15A, according to one embodiment.

Figure 24A:
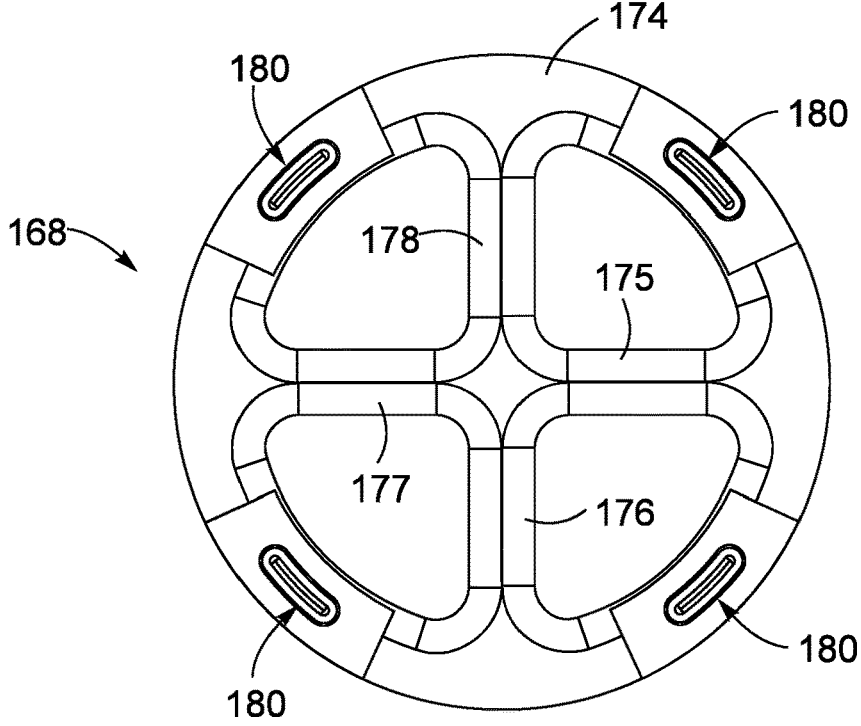
Figure 24B:
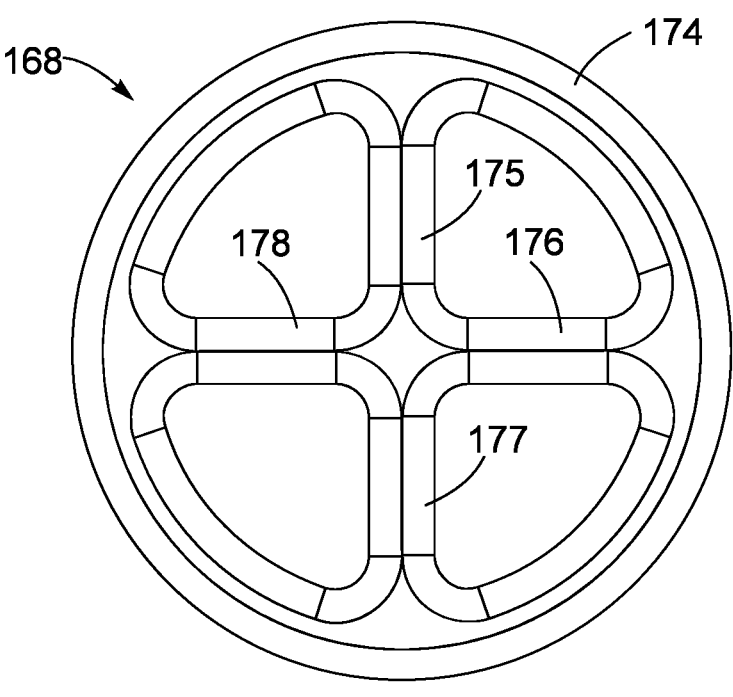

FIGS. 24A and 24B are top and bottom plan views, respectively, of a first frame member of the frame member of FIG. 23.

Figure 25:
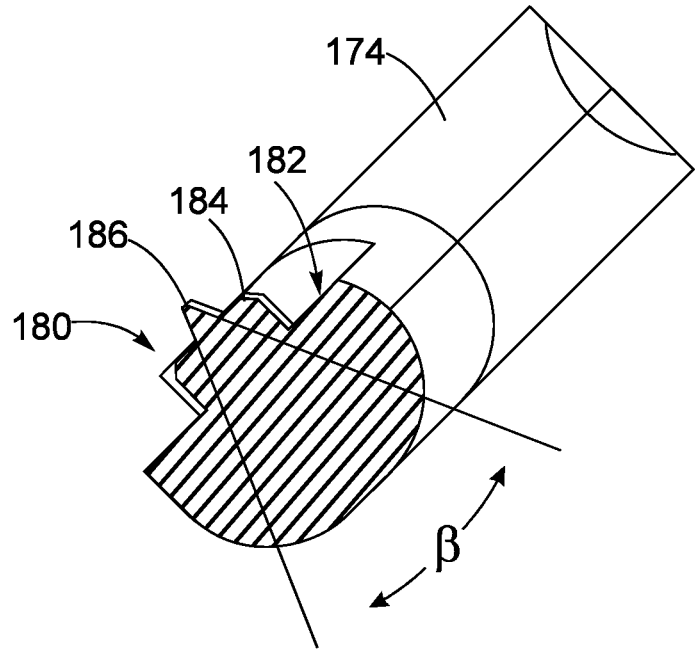

FIG. 25 is a cross-sectional view of a portion of the first frame member illustrating a coupling portion.

Figure 26:
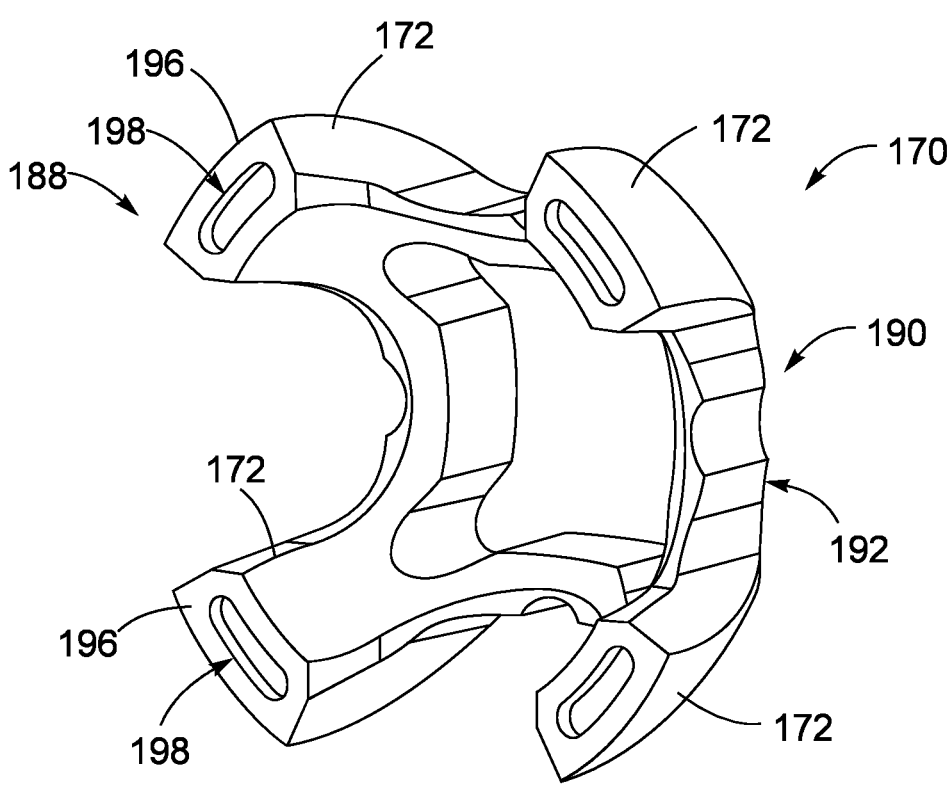
Figure 27:
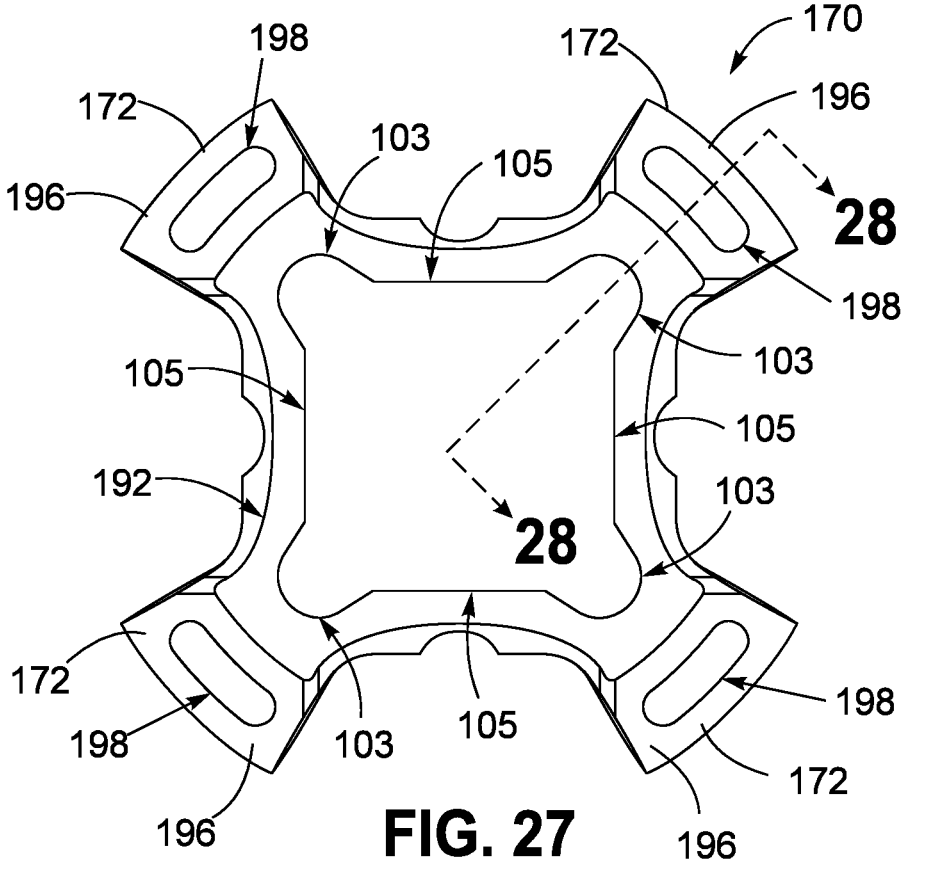

FIGS. 26 and 27 are a perspective view and a top plan view, respectively, of a second frame member of the frame member of FIG. 23, according to one embodiment.

Figure 28:
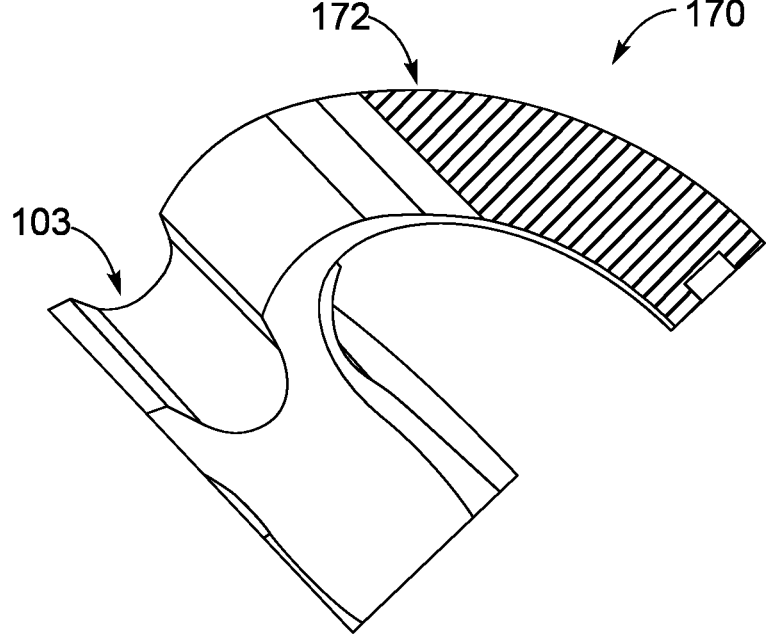

FIG. 28 is a cross-sectional view of the second frame member taken along line 28-28 of FIG. 27.

Figure 29:
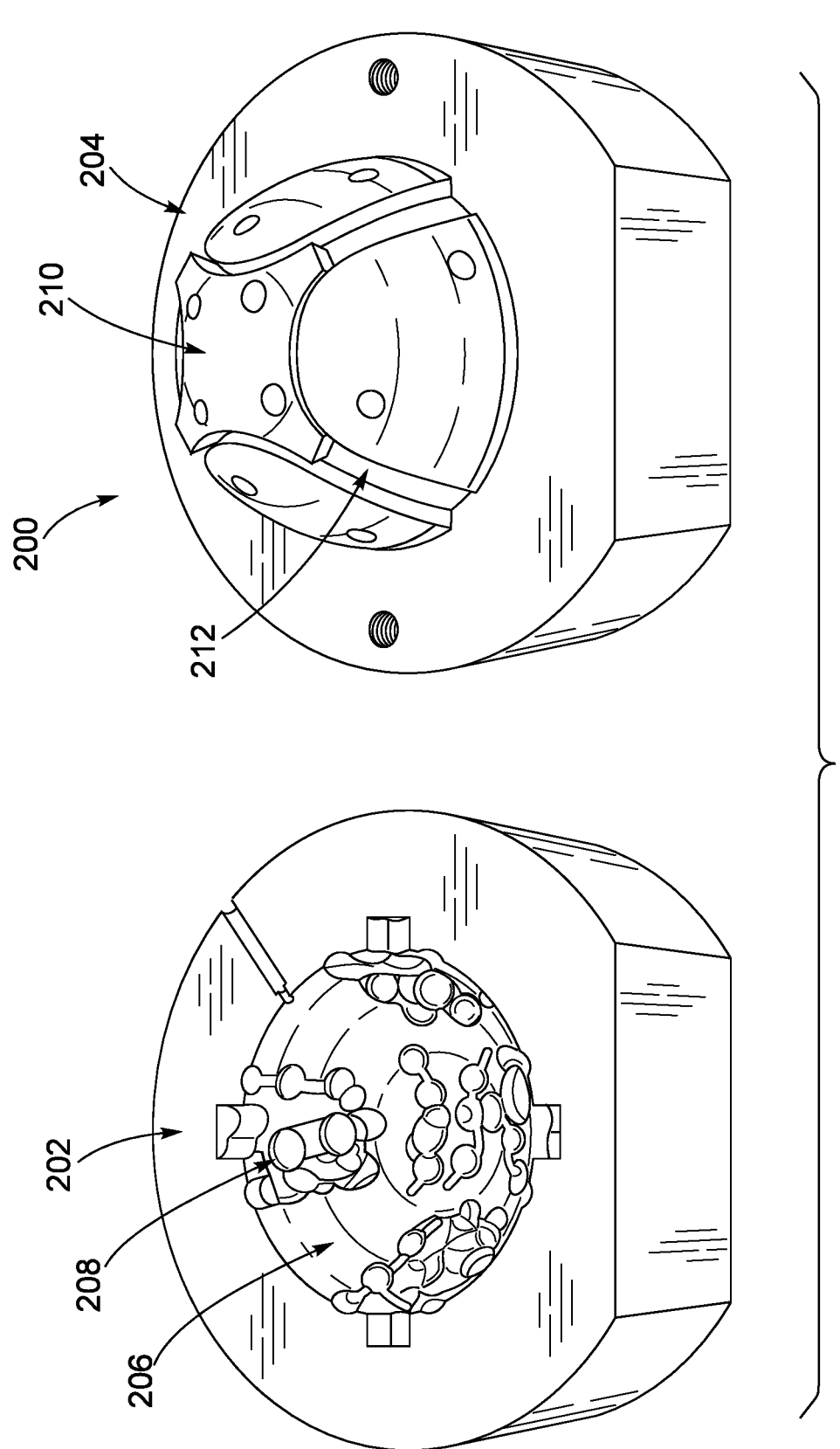

FIG. 29 is a perspective view of a molding apparatus for producing a frame of a hemispherical cutting tool, according to one embodiment.

FIG. 30 is a perspective of an arrangement of panels for a hemispherical cutting tool, according to another embodiment.

FIG. 31 is a perspective view of a portion of a frame to which the panels in FIG. 30 can be coupled.

FIG. 32 is a perspective view of a hemispherical cutting tool, according to another embodiment.

Figure 33:
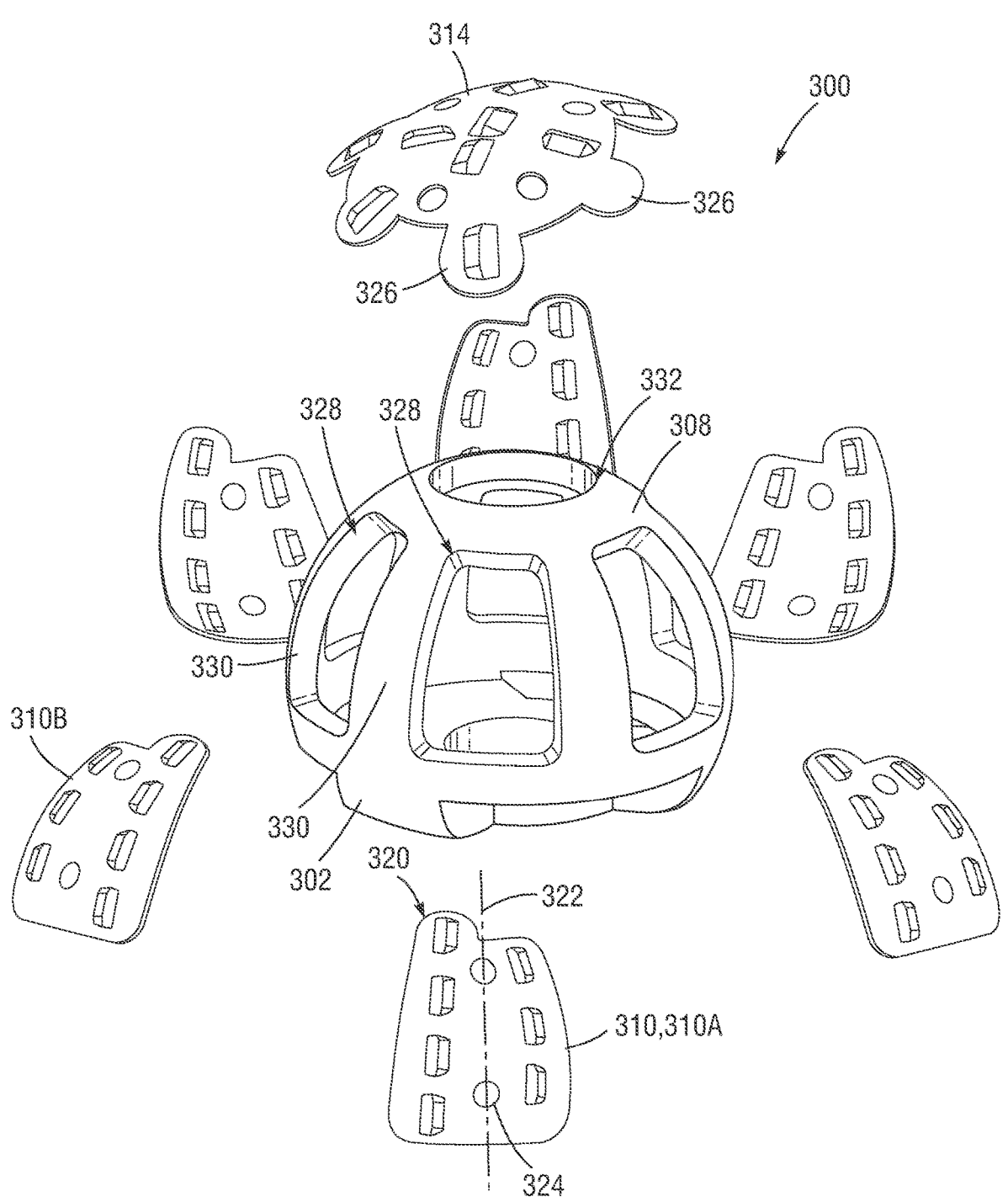

FIG. 33 is an exploded view of the hemispherical cutting tool of FIG. 32.

DETAILED DESCRIPTION

General Considerations

The following description is exemplary in nature and is not intended to limit the scope, applicability, or configuration of the present disclosure in any way. Various changes to the described embodiments may be made in the function and arrangement of the elements described herein without departing from the scope of the disclosure.

Although the operations of some of the disclosed embodiments are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art when viewed in light of this disclosure.

It should be understood that the disclosed embodiments can be adapted to prepare orthopedic surgery other than hip implantation. For example, the disclosed systems and methods can be adapted for preparation of prosthetic shoulder implantation or other surgical procedures.

As used herein, the term "proximal" refers to a position, direction, or portion of a device that is closer to the user and further away from the implantation/surgical site. As used herein, the term "distal" refers to a position, direction, or portion of a device that is further away from the user and closer to the implantation/surgical site. Thus, for example, proximal motion of a device is motion of the device away from the implantation/surgical site and toward the user (e.g., out of the patient's body), while distal motion of the device is motion of the device away from the user and toward the implantation/surgical site (e.g., into the patient's body). The terms "longitudinal" and "axial" refer to an axis extending in the proximal and distal directions, unless otherwise expressly defined.

As used herein, the term "approximately" and "about" means the listed value and any value that is within 10% of the listed value. For example, "about 10 mm" means any value between 9-11 mm, inclusive.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

As used herein, the term "effective functional life" means the amount of use a tool can experience before it begins to operate sub-optimally for its intended purpose. In some embodiments, the effective functional life can be based on a number of uses of the tool and/or an amount of time the tool has been used. As used herein, the term "powered driving member" means any device capable of driving a cutting tool such as, for example, a drill.

As used herein, the term "single use" tool or instrument means a tool or instrument that is configured and/or intended to be used once before being discarded. Thus, a single use tool or instrument can be a non-reusable device in contrast to reusable tools or instruments which, subject to certain procedures such as cleaning and sterilization, may be used more than once. As used herein, the term "disposable" device or instrument means a device or instrument that is configured and/or intended to be used one or a few times before being discarded.

As used herein, the term "spherical reamer" is used interchangeably with the term "hemispherical reamer" unless the context clearly indicates otherwise.

Directions and other relative references may be used herein to facilitate discussion of the drawings and principles described herein. For example, certain terms may be used such as "up," "down,", "left," "right," "horizontal," "vertical," and the like. Such terms are used, where applicable, to provide some clarity of description when dealing with relative relationships, particularly with respect to the illustrated embodiments. Such terms are not, however, intended to imply absolute relationships, positions, and/or orientations. As used herein, "and/or" means "and" or "or", as well as "and" and "or".

Cutting Tools

Figure 1:
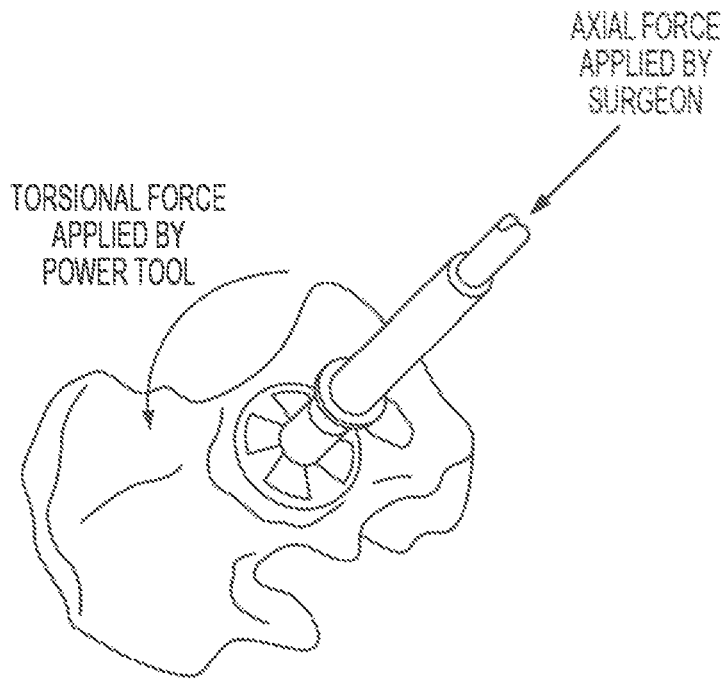
FIG. 1 illustrates an acetabular reamer, and the use of the reamer to prepare the acetabulum, for example axial force applied by a surgeon by pushing the cutter into the acetabulum and a second torsional force exerted by the power reaming tool as part of a total hip procedure, according to one embodiment.

It is generally desirable that cutting surfaces on a cutting tool (e.g., cutting teeth) be as accurate and consistent as possible for the dimensional accuracy of the final preparation in the bone. For example, cementless acetabular implants (press fit) are dependent on their dimension and the dimension of the bone preparation to create a reproducible interference fit for establishing initial stability of the implant. FIG. 1 illustrates an acetabular reamer and use of the reamer to prepare the acetabulum, including axial force applied by the surgeon and torsional force applied by the power tool.

The initial stability of the implant is critical to long term success and if the implant moves large amounts (e.g., 75 microns or more) under physiological loads post-operatively, it can result in soft tissue growing into the implant rather than bone. If this occurs, the implant will eventually loosen. Accordingly, the accuracy of the initial fit must provide stability of the implant to allow bone to grow into the implant during the first 6-12 weeks after surgery. In some instances, the interference level required for cementless acetabular implants can be required to be very small (e.g., less than 2 mm, and, in some cases, preferably less than 1 mm). However, commercial cutters can vary in their accuracy by as much as 0.25 mm and these variations can result in initial acetabular implant stability. Because the initial interference fit provides stability to the implant, improved accuracy of the teeth height and performance can assist in achieving this goal.

Configuration of Cutting Members

Conventional reamer designs use the same cutting tooth geometry within each design. These teeth are also positioned at 90° to the latitude lines of the spherical reamer surface. However, cutting teeth around the equator of the reamer perform a side cutting function while teeth towards the dome of the cutter perform an end cutting function.

As described in more detail herein, various embodiments are provided in which reamers utilize different cutting teeth configurations and different orientations to address the different bone cutting requirements and thereby improving the efficiency of the cut. By efficiently designing cutting teeth for specific operations, faster bone cuts can be achieved, thereby producing less friction. Minimizing the friction generated by the reamers relates directly to maintaining the life of the bone. Friction can lead to heat and if the cutter-bone interface reaches temperatures above 50° C. (122° F.) bone death (necrosis) can occur. This can affect long term success of the procedure whether the implant is used with or without bone cement. If the bone preparation bed is damaged due to excessive heat generated from the acetabular cutter, the fixation of the implant will be compromised and can lead to loosening and revision.

Figure 2C:
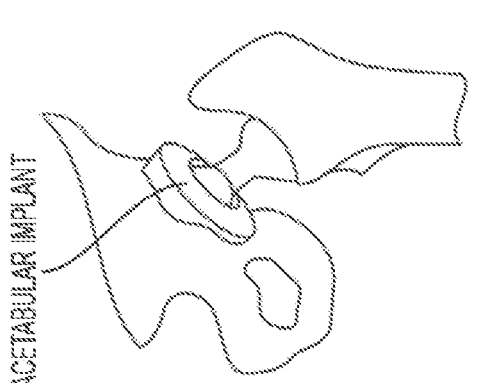
FIG. 2C illustrates the acetabular implant in position as part of a total hip procedure.
Figure 2B:
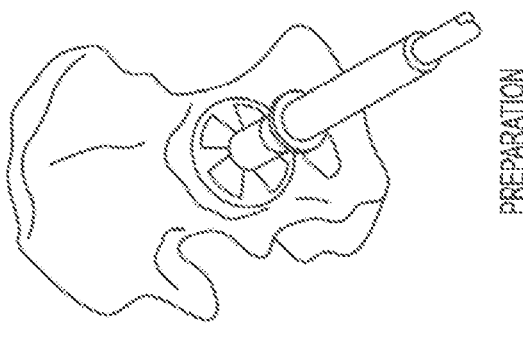
FIG. 2B illustrates use of the reamer to prepare the acetabulum.
Figure 2A:
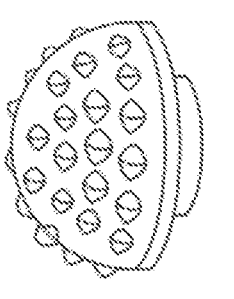
FIG. 2A illustrates an acetabular reamer with a hollow spherical cutter.

There are two primary forces applied to the reamer during the machining of the bone. When considering an acetabular reamer, as shown in FIGS. 1 and 2A-2C, there is an axial force applied by the surgeon who pushes the cutter into the acetabulum and a second torsional force exerted by the power reaming tool. In some embodiments, the cutting tools disclosed herein convert the torsional force into a force applied at the cutting tooth edge to improve the efficiency of the cut. FIG. 2A illustrates an acetabular reamer with a hollow spherical cutter. FIG. 2B illustrates use of an acetabular reamer to prepare the acetabulum, and FIG. 2C illustrates an acetabular implant press fit in the prepared acetabulum as part of a total hip replacement procedure.

The systems and methods described herein for forming cutting tools can provide greater control and accuracy of the tooth sharpness, cutting angles, and resulting bone chip removal by the tool. In addition, as described in more detail below, the cutting tools described herein can be formed by manufacturing processes that permit the creation of multiple teeth in one operation.

Figures 3A, 3B, 3C:
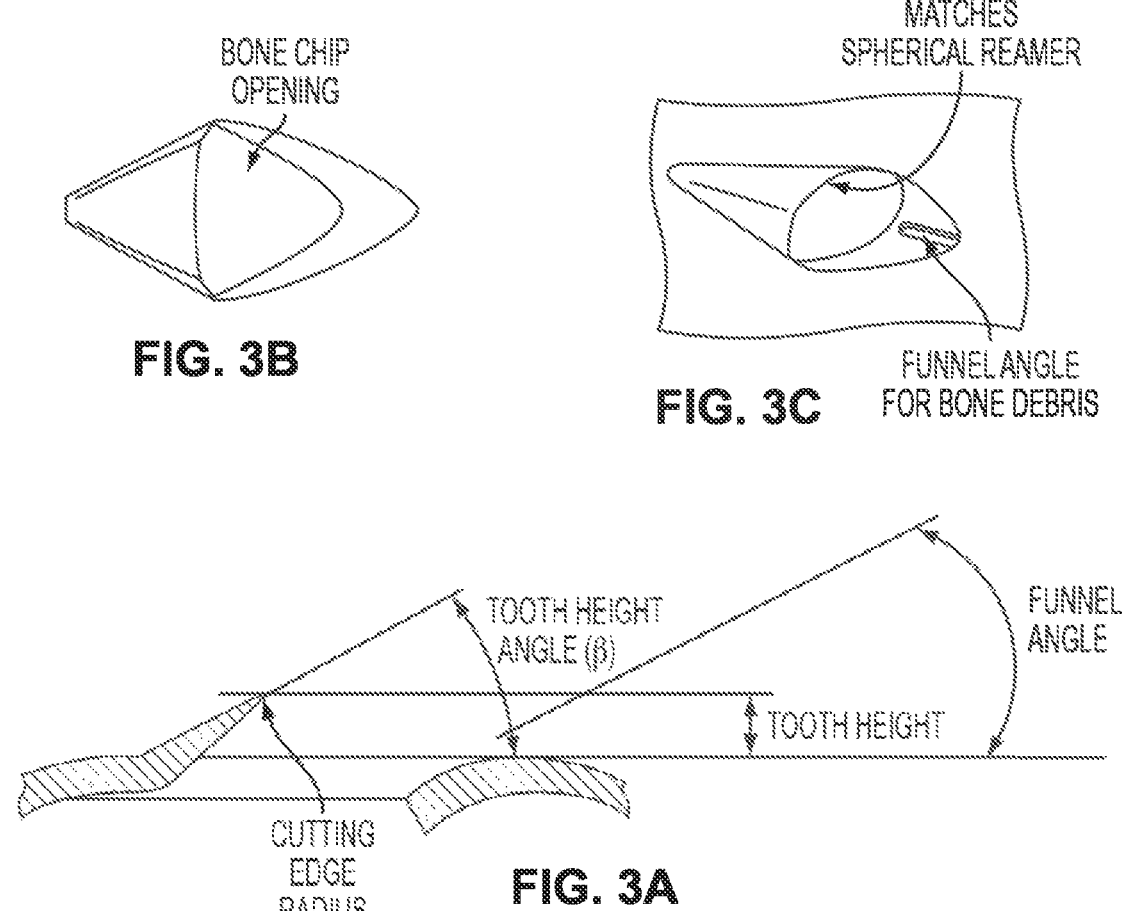
FIG. 3A illustrates a cutting tool composed of a sharp tooth edge, a specific tooth elevation, specific cutting angle, a specific tooth orientation to the axis of rotation and a peripheral opening around the cutting edge providing an improved flow path for the bone debris.
FIG. 3B illustrates a bone chip opening.
FIG. 3C illustrates a funnel angle for bone debris and a radial cutting edge that matches the spherical reamer.
Figures 4A, 4B, 4C:
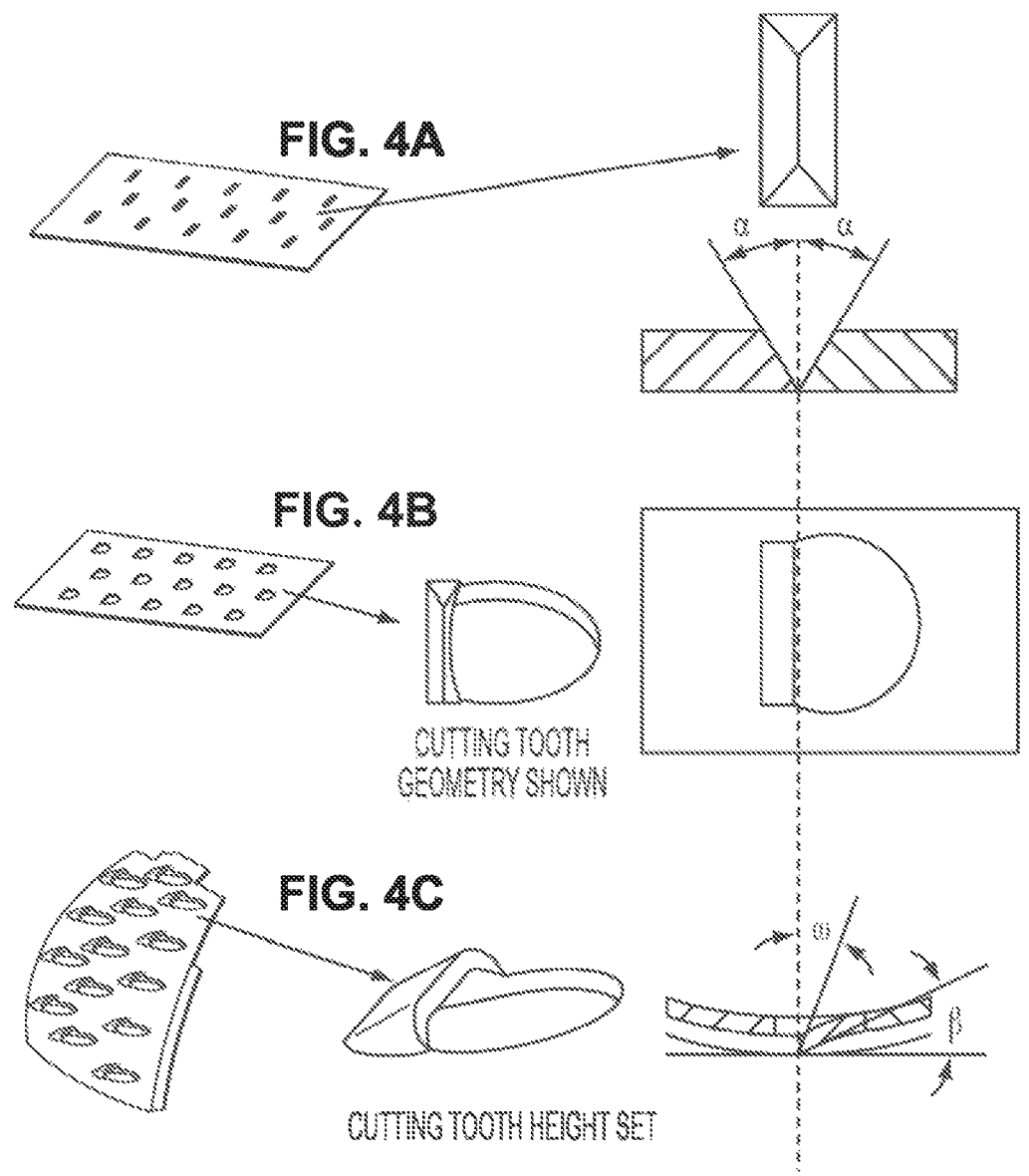
FIG. 4A illustrates a manufacture of cutting teeth geometry by forming a sheet.
FIG. 4B illustrates cutting tooth geometry of the sheet.
FIG. 4C illustrates a cutting tooth height set.

In the embodiments described herein, cutting surfaces (e.g., teeth) can comprise a sharp tooth edge (tolerance 0.0005" to 0.002" (0.013 mm to 0.051 mm) tooth edge radius), a specific tooth elevation (tolerance 0.002"-0.004" (0.051 mm to 0.11 mm)), specific cutting angle, a specific tooth orientation to the axis of rotation (e.g., tool angle), and a peripheral opening around the cutting edge providing a designed flow path for the bone debris as shown in FIGS. 3A-3C. This tooth geometry can also be manufactured according to FIGS. 4A-4C through a series of stamping operations allowing for multiple teeth to be made at the same time. For example, as illustrated in FIG. 4A, a flat sheet of material (e.g., metal) can be stamped so that a plurality of "V"-type cavities are punched into the sheet based on a desired cutting angle ω. Next, a plurality of holes can be punched around the "V"-type cavities (or grooves), creating a cutting edge, as shown in FIG. 4B. If necessary, another stamping step can be performed to stamp the tooth height and curvature in operation (or multiple operations if desired). As shown in FIG. 4C, angle β determines the tooth height and angle β in conjunction with angle α (FIG. 4A) will determine the rake angle ω ($\omega=\alpha-\beta$) of the cutting surface. In some embodiments, the rake angle can vary between about 5 and 25 degrees, and in other embodiments between about 5 and 15 degrees (e.g., about 10 degrees)

Thus, in contrast to conventional devices, the tooth angle (α) can be established in the first forming operation and can be set (ω and β angles) based on the intended function. Multiple iterations of this tooth design can be provided in specific zones of the reamer surface which address the intended type of cutting required at those locations.

Figures 5A, 5B:
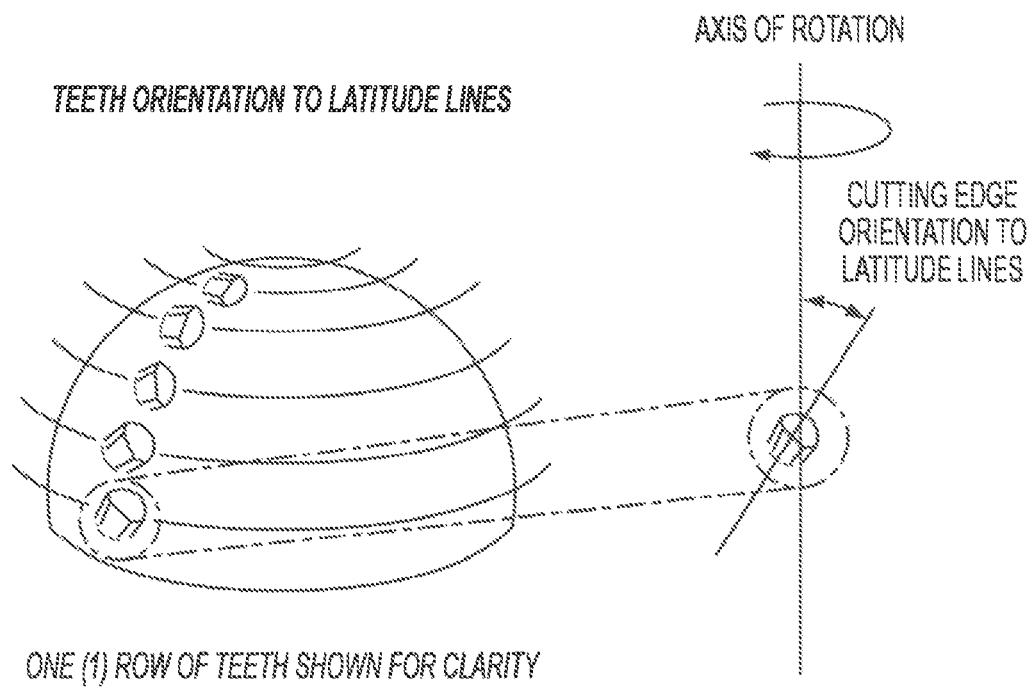
FIG. 5A illustrates a cutting tool having a plurality of teeth, with one row of teeth shown for clarity.
FIG. 5B illustrates the cutting edge orientation to latitude lines and an axis of rotation of the cutting tool.
Figure 6:
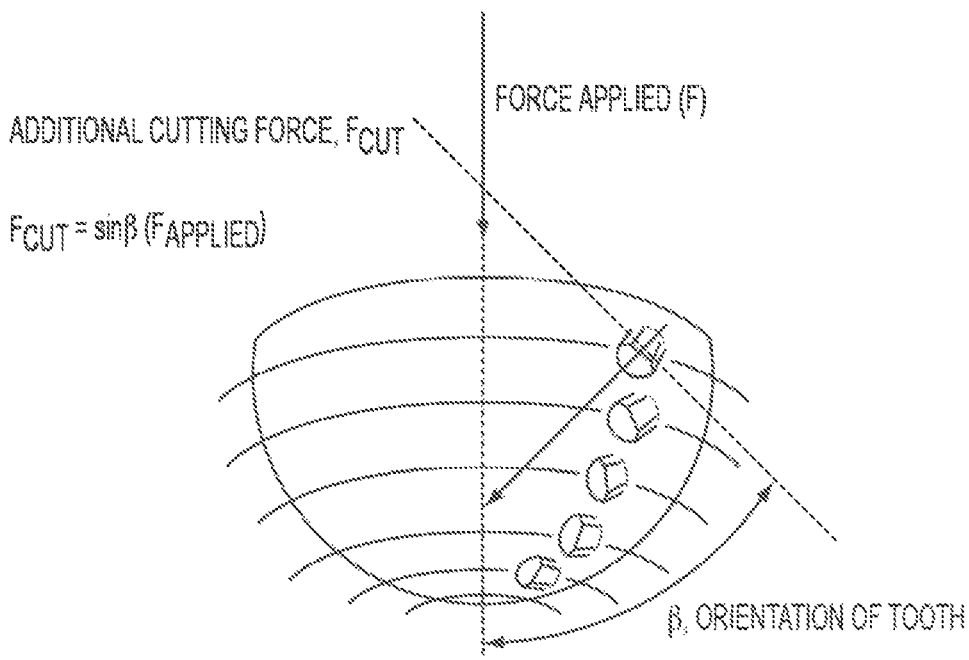
FIG. 6 illustrates a cutting tool having a plurality of teeth.

In some embodiments, the cutting tools disclosed herein can have teeth arranged in a spiral or helix manner on the surface of the cutter. However, the tooth designs and tooth orientations can be optimized to reduce the reaming time required to complete the preparation. As shown in FIGS. 5A-8D, the cutting edges of the teeth can be oriented at different angles to the lines of latitude based on the required cutting functions at various positions on the surface of the reamer. This can provide for a faster cut by converting the rotational energy into linear energy assisting in advancing the reamer into the preparation analogous to a screw thread (FIGS. 5A-5B). FIG. 5A shows the orientation of teeth of one row of teeth relative to latitude lines for clarity. FIG. 5B shows the cutting edge orientation of a single tooth to latitude lines and the axis of rotation of the cutting tool. The tooth orientation can further improve the cutting force at the tooth edge. By changing the orientation of the cutting edge relative to the latitude lines, a portion of the torsional force is converted into a cutting force at the tooth edge as shown in FIG. 6. This improvement primarily benefits the teeth closest to the equator as they are performing a side cutting function. In FIG. 6, the angle β is the orientation of the tooth, the force F applied is represented as a downward arrow, and the additional cutting force $F_{cut}$ is given by the equation $F_{cut}=\sin(F_{Applied})$. In certain embodiments, teeth orientation to latitude lines improved cutting force at the tooth edge.

As shown in FIGS. 5A-6, the angle of orientation of the cutting edge relative to axis of rotation can increase from the equatorial teeth to the polar teeth and decrease relative to the latitude lines. At least three different types of cutting teeth (e.g., orientation angles and/or cutting angles varying) can be provided on the tool. In some embodiments, at least three regions are provided with similar type teeth in each region. In other embodiments, the teeth can vary in a transitional manner effectively providing more than three zones.

In some embodiments, relative to the latitude lines, the range of variation can be orientation angles of between 10 and 30 degrees (more preferably between 15 and 25 degrees—e.g., 20 degrees) for the equatorial zone, orientation angles of less than 5 degrees (more preferably about 0 degrees) in the polar zone, and somewhere in between for the orientation angles in the transition zone (e.g., between 0 and 20 degrees, or preferably between 5 and 15 degrees—

11 e.g., 10 degrees). A benefit of the larger orientation angles in the equatorial zone is a portion of the axial load applied by the operator will be converted into driving the cutting edge into the bone. As you move to the polar zone, the angle of the tooth on the surface has less effect as the tooth becomes perpendicular to the direction of the cut. That is, the specific tooth geometry in the polar zone needs to address an end cutting ability rather than a side cutting ability.

FIGS. 7A-7E illustrate an exemplary process by which a cutting tool (e.g., a spherical reamer) transitions from engagement with the bone at one area to another area of the cutting tool. As used herein, the term "polar teeth" refer to cutting surfaces at and/or adjacent the pole of the spherical reamer, the term "equatorial teeth" refer to cutting surfaces at and/or adjacent to the equator of reamers having a hemispherical shape (e.g., the area furthest from the poles in FIGS. 7A-7E), and the term "transition teeth" refer to cutting surfaces between the polar and equatorial teeth.

Figures 7A, 7B, 7C, 7D, 7E:
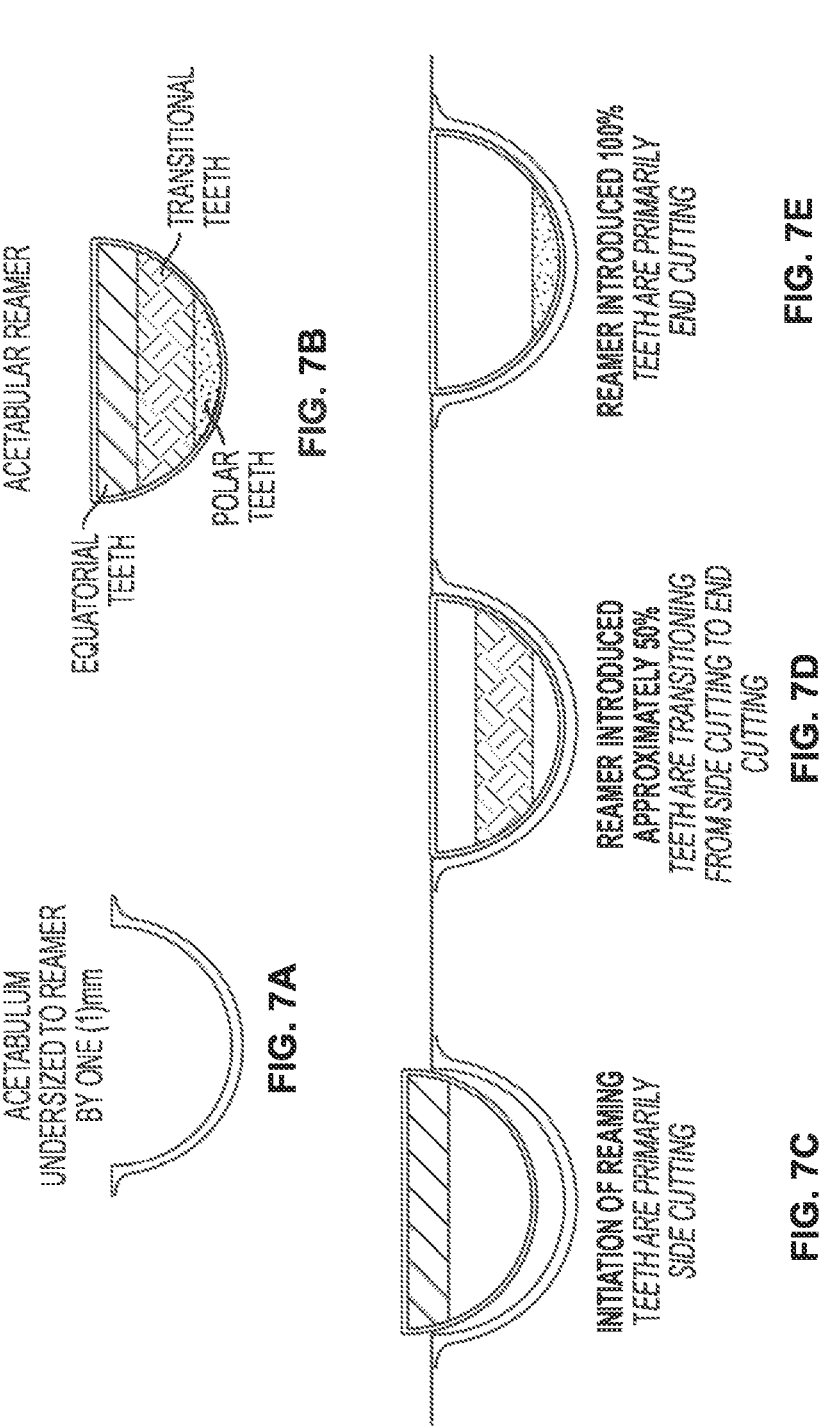
FIG. 7A illustrates an acetabulum undersized to a reamer.
FIG. 7B illustrates a schematic view of cutting teeth zones.
FIG. 7C illustrates a primarily side cutting reaming action.
FIG. 7D illustrates a transition from side cutting to end cutting.
FIG. 7E illustrate a primarily end cutting action.

In the exemplary reaming process illustrated in FIGS. 7A-7E, the spherical reamer begins by introduction into the concave surface of the acetabulum (FIG. 7C). It is noted that this initiation of the cut involves just the equatorial teeth. These equatorial teeth are performing more of a side cutting function and therefore can have a specific tooth angle based on this intended function. Additional teeth (i.e., the transitional teeth) become engaged with the bone as the reamer is further introduced into the acetabulum. For example, in FIG. 7D the reamer is introduced approximately 50% and the teeth are transitioning from side cutting to end cutting. The transitional teeth perform a combination of side-cutting and end-cutting and can be optimized for this purpose. As the reamer becomes fully inserted into the preparation site (FIG. 7E), the teeth at the pole (i.e., the polar teeth) of the reamer serve to primarily end-cut.

Thus, the teeth can have different cutting demands depending on their location on the surface of the reamer and can be configured accordingly. FIGS. 8A-8D illustrate the manner in which the cutting angles of the teeth can vary in accordance with the required cutting function of the bone. The table below illustrates the types of teeth and their configurations as reflected in FIGS. 8A-8D.

12 edge radius, funnel angle, or tooth height, whereas the teeth in two adjacent zones can have different tooth edge radius, funnel angle, or tooth height.

In alternative embodiments, the teeth in each of the three zones can vary in characteristics (cutting angles, tooth edge radius, funnel angle, tooth height, etc.). For example, the cutting surfaces can transition gradually from one zone to another. Thus, polar teeth can transition gradually from polar teeth with the orientation and characteristics noted above to transition teeth with the orientation and characteristics noted above. In this manner, for example, some teeth can have orientation and characteristics of polar teeth (e.g., 65 degree cutting angle), some can have characteristics of transition teeth (e.g., 45 degree cutting angle), and some teeth between the polar teeth and transition teeth can have characteristics somewhere inbetween (e.g., 55 degree cutting angle). In one example, the cutting angle in the polar zone may gradually decrease from about 70 degrees at the pole region to about 60 degrees at the polar-transition zone boundary; the cutting angle in the transition zone may gradually decrease from about 50 degrees at the polar-transition zone boundary to about 40 degrees at the transition-equatorial zone boundary; and the cutting angle in the equatorial zone can gradually decrease from about 30 degrees at the transition-equatorial zone boundary to about 20 degrees at the equatorial region.

Proper bone chip exit paths can also contribute to an improved surgical preparation. With a non-impeded path for the bone chips to travel away from the cutter, it enables the instrument to produce a faster and cooler bone cut. As shown in FIGS. 3A-3C, openings can be provided adjacent cutting surfaces to provide a "funnel" that permits bone chips to efficiently flow from the face of the reamer to avoid additional torque requirements to drive the cutter. Without such openings, increased torque is required to drive the cutting tool and such increased torque is usually accompanied by increased axial pressure as the operator senses the resistance in advancing the cutter and applies increased loads. This combination generates increased heat through friction capable of generating temperatures which can cause bone necrosis.

Manufacturing of Cutting Tools

| Teeth Region | Cutting angle (defined relative to a side surface of the cutting tool) | Tooth edge radius | Funnel angle | Tooth height |
|---|---|---|---|---|
| Equatorial | 15-35 degrees (more preferably, 20-30 degrees) | 0.0005-0.002" (0.013 mm-0.051 mm) | 20-40 degrees, (more preferably, 25-35 degrees) | 0.020" (0.51 mm) ± 0.002" (0.051 mm) |
| Transition | 35-55 degrees (more preferably, 40-50 degrees) | 0.0005-0.002" (0.013 mm-0.051 mm) | 20-40 degrees, (more preferably, 25-35 degrees) | 0.020" (0.51 mm) ± 0.002" (0.051 mm) |
| Polar | 55-75 degrees (more preferably, 60-70 degrees) | 0.0005-0.002" (0.013 mm-0.051 mm) | 20-40 degrees, (more preferably, 25-35 degrees) | 0.020" (0.51 mm) ± 0.002" (0.051 mm) |

Figure 9:
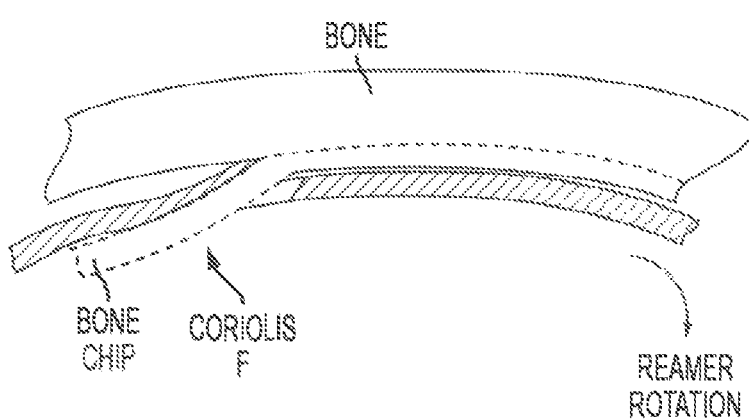
FIG. 9 illustrates a schematic view of cutting forces applied by a cutting tool.

In certain embodiments, the teeth in each of the three zones can generally have the same characteristics, whereas the teeth in two adjacent zones can have different characteristics. For example, the teeth in each zone can have the same cutting angle, whereas the teeth in two adjacent zones can have different cutting angles. In one exemplary embodiment, the teeth in the equatorial zone can have the same first cutting angle (e.g., 25 degrees), the teeth in the transition zone can have the same second cutting angle (e.g., 45 degrees), and the teeth in the polar zone can have the same third cutting angle (e.g., 65 degrees). Similarly, the teeth in each of the three zones can generally have the same tooth In some embodiments, the cutting tools can be manufactured by forming the spherical body and teeth from thinner sheet metal, 0.005"-0.020" (0.127 mm to 0.51 mm), which can improve the efficiency in manufacturing (longer tool life of the forming tools) and ability to create a sharp tooth edge without a specific sharpening operation. In addition the thinner material better dissipates the heat generated from the friction of cutting the bone over a thicker walled, heavier mass reamer. The thinner material also produces less friction, therefore a lower temperature at the surface (friction heating), through reduction of the Coriolis forces (FIG. 9). With reference to FIG. 9, the Coriolis force can be given by the equation $F_c=-2m\Omega(v)$, where m is the mass of the reamer, $\Omega$ is the angular velocity vector, and v is the velocity of the rotating system.

Figure 10A:
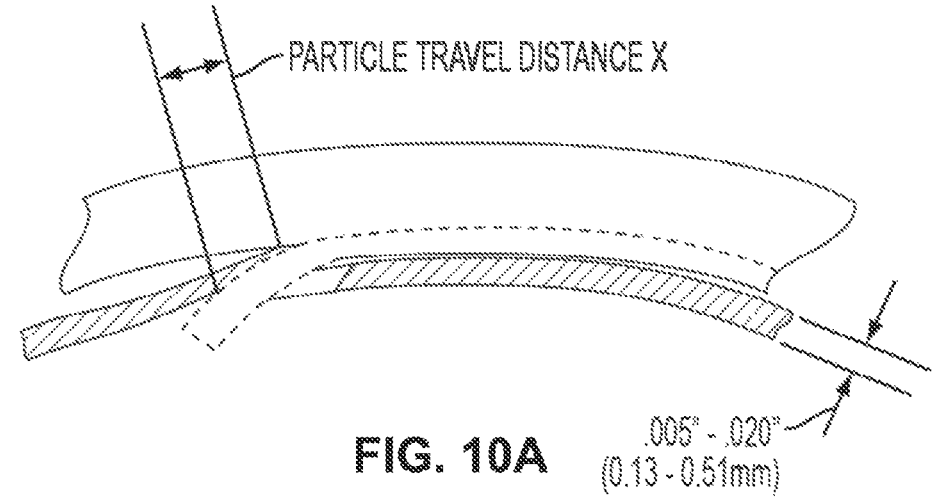
FIG. 10A illustrates frictional forces associated with bone chips created by a cutting tool with a first thickness.
Figure 10B:
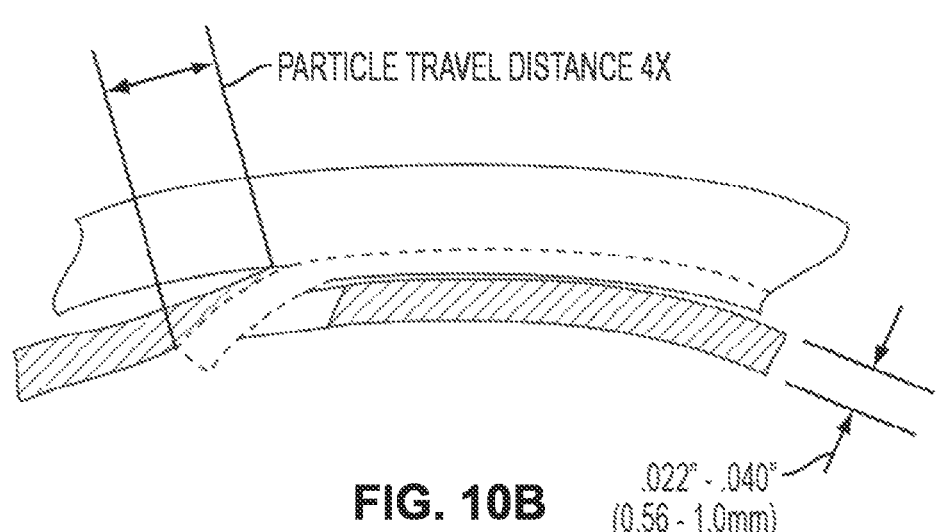
FIG. 10B illustrates frictional forces associated with bone chips created by a cutting tool with a second thickness.

FIGS. 10A and 10B illustrate a comparison of the frictional forces associated with bone chips created by cutting tools having different thicknesses. As shown in FIG. 10B, for thicker walled cutters (e.g., cutters with wall thicknesses greater than 0.022" (0.56 mm)), the bone chip particles must travel a greater distance in contact with the cutting surface of the cutter. As a result, lower temperatures can be achieved by producing cutters with wall thickness of between 0.005" and 0.020" (0.127 mm and 0.51 mm). As shown in FIGS. 10A and 10B, a cutter with a wall thickness of 0.56 mm to 1 mm can result in a particle travel distance four times greater than the particle travel distance of a cutter with a wall thickness of 0.127 mm and 0.51 mm. The following manufacturing methods can be used to produce cutting tools with such reduced wall thicknesses.

Using the manufacturing techniques described herein, any number of teeth (e.g., 1-20 or more) can be made in a single forming step. In contrast, conventional systems require multiple forming steps for each individual tooth. Because the number of operations required to manufacture a spherical reamer can be greatly reduced, the costs are similarly reduced, thereby providing a lower cost, yet equally effective, cutting tool that can be removed from clinical service at a the end of its functional life without significant financial loss.

Figure 11A:
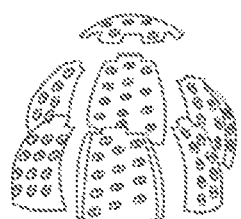
FIG. 11A illustrates stamped cutting panels of a spherical reamer.
Figure 11B:
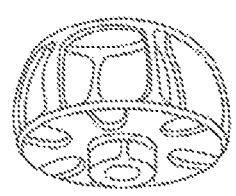
FIG. 11B illustrates an injection molding tool for creating plastic framing.
Figure 11C:
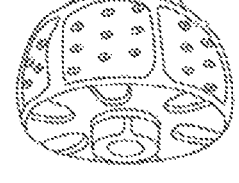
FIG. 11C illustrates a finished reamer.

It should be understood that the supporting structure for the panels can be formed in various manners. For example, FIGS. 11A-11C illustrate an alternative approach in which the panels are secured by a plastic molded part. FIG. 11A illustrates the stamped cutting panels. FIG. 11B illustrates a representative plastic frame that can be injection molded around the stamped metal panels of FIG. 11A. FIG. 11C illustrates a finished reamer formed by this process that is structurally sound through the frame and maintains cutter sphericity and tolerances with 0.004 inch (0.1 mm)

In some embodiments, the panels are placed directly into an injection molding tool and a medical grade plastic (e.g., PEI (polyetherimide, ULTEM®), PEEK (polyetheretherketone), PAI (polyamidide, TORLON®) can be injected around the periphery of the panels creating a frame that encloses and secures the panels.

The cutting tools can be color coded to facilitate identification of the various sizes and types of cutting tools. When the cutting tool frames are formed by injection molding, such color coding can be achieved by varying the color of the injection molded plastic part.

Figure 13:
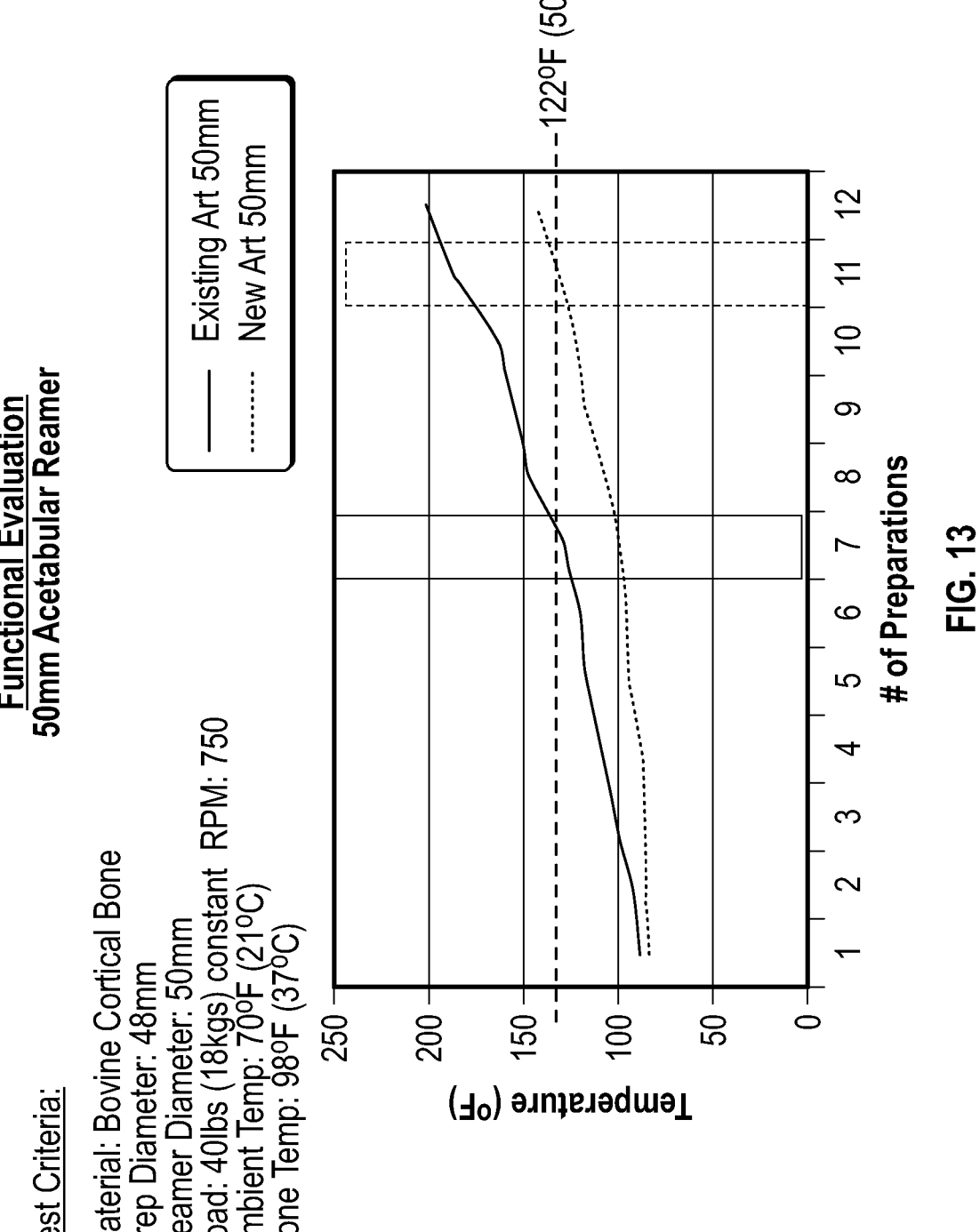
FIG. 13 illustrates the results of an exemplary test procedure.

Laboratory testing of a disclosed embodiment provided a comparison to existing art spherical reamers. Bovine bone specimens were used to monitor the speed to prepare a standard preparation, the temperature generated during that preparation and how many preparations could be completed before cutting edge damage generated a temperature exposure to the bone above 50° C. (122° F.). FIG. 13 summarizes the results of this testing and illustrates some of the improvements, such as the ability to cut bone at a lower temperature for a greater number of uses.

All cutting tools will eventually wear at the cutting edges resulting in a non-efficient cutter which would need to be sharpened or discarded. This is true of all industries including the medical field where these cutters are machining bone. In this field, the consequences of the cutter becoming dull and continuing to use it can result in bone necrosis. This in turn can jeopardize the success of the surgical procedure as the prosthesis must be supported by live, healthy bone to stabilize the implant. Excessive heat will kill the bone leading to bone resorption and a less than ideal interference fit between the bone and the implant. The rounding of the teeth cutting edges and damage to these edges can be demonstrated after 4-6 uses of these reamers in cow bone. It is for that reason all cutters should be qualified through laboratory testing to define the maximum number of uses under worst-case conditions which will not violate the temperature threshold for killing bone. This test result can then be used as a method to identify when the cutter should be removed from use.

FIG. 13 illustrates the results of an exemplary test procedure in a laboratory test set-up for determining the effective functional life of a cutting tool. In these tests, acetabular reamers were used to cut bone (i.e., cortical bovine bone) to determine the number of uses the acetabular reamers can experience before the end of their effective functional life. In one example, it was determined that approximately six (6) uses of the reamer produces a complete preparation without generating excessive heat (e.g., temperatures at or above 122° F. (50° C.)).

Figure 14:
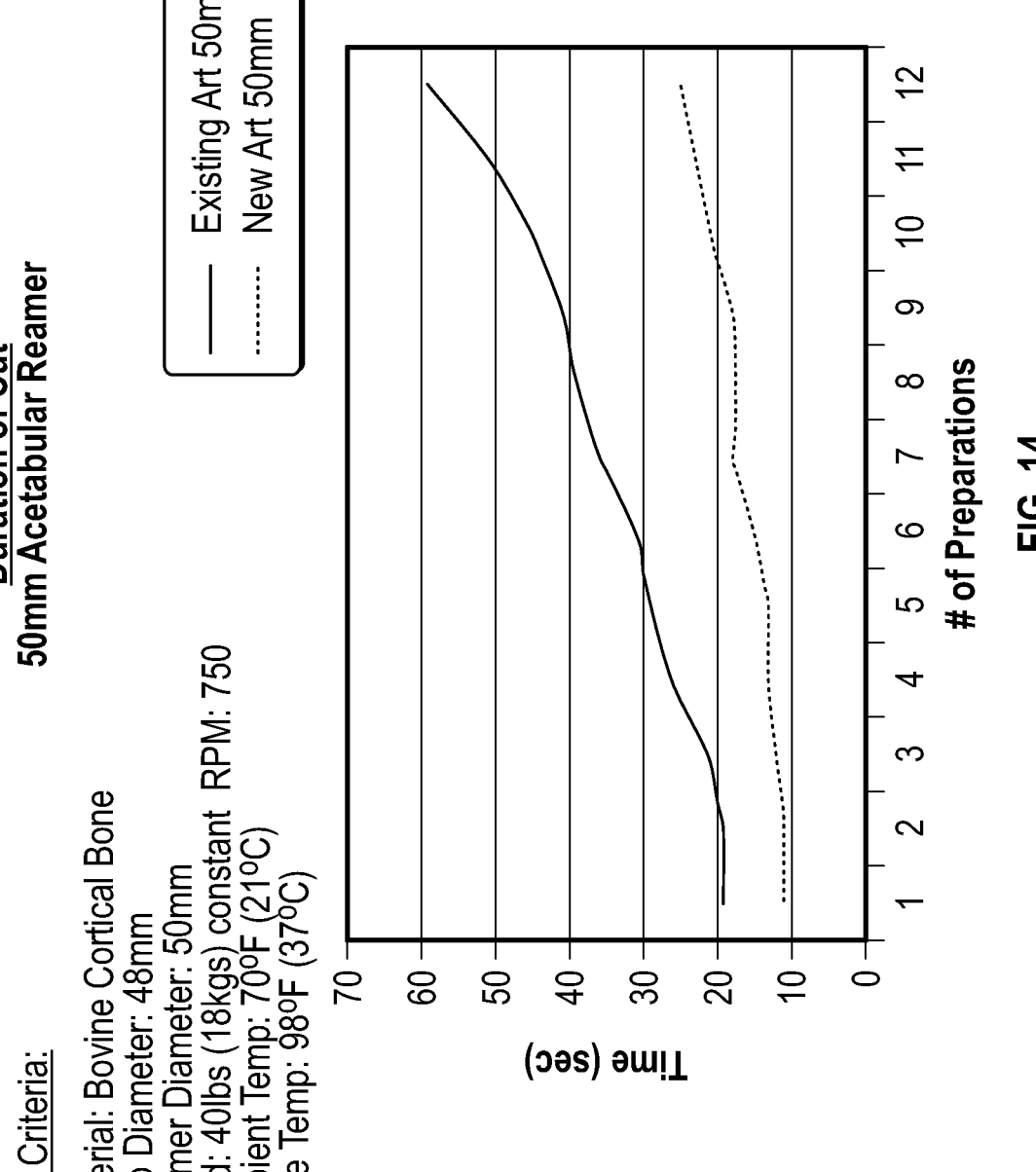
FIG. 14 illustrates the results of an exemplary test procedure.

FIGS. 13-14 also illustrate the results of an acetabular reamer evaluation in bovine bone, including (1) a chart showing the functional evaluation of a 50 mm acetabular reamer to cut bovine bone, graphing the number of bone preparations (i.e., uses of the cutting tool) and the temperature in the bone preparation area (FIG. 13); and (2) a chart showing the functional evaluation of a 50 mm acetabular reamer to cut bovine bone, graphing the number of bone preparations (i.e., uses of the cutting tool) and the time required to achieve the bone preparation (FIG. 14). As shown in FIG. 13, continuing to use the cutter after the sixth use consistently resulted in a longer preparation time and increased heat generation. The sharpness of the teeth cutting edges are directly proportional to the load required to advance the cutter, and therefore the resulting friction/heat generated. As the cutting edge rounds (or dulls), it becomes less effective in penetrating the surface of the bone and requires additional load to attempt to advance it. This cutter wear is generally consistent for all cutting tools.

Figure 12:
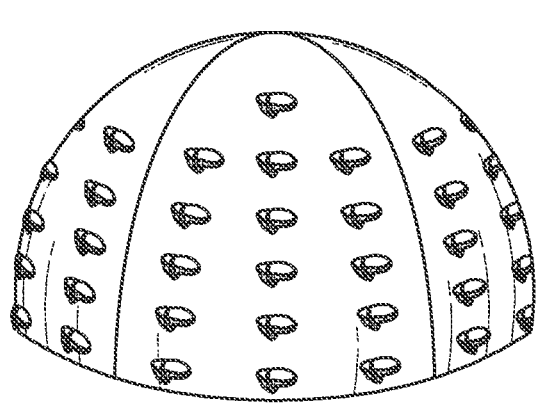
FIG. 12 illustrates another embodiment of a spherical reamer.

FIG. 12 illustrates another exemplary cutting tool configured as a hemispherical reamer. The cutting tools and methods of manufacturing the same can provide a number of improvements, including (in certain embodiments) at least some of the following improvements:

1. Multiple teeth designs and teeth orientations to address multiple machining needs of the bone yielding a faster, cooler cut.
2. Tooth design geometries which address side cutting, end cutting and a combination of both.
3. A thinner material for forming the spherical reamer which can improve sharpness and reduction of heat.
4. A thinner material which also provides for more efficient forming of teeth and component parts improving manufacturing tool life.
5. Ability to produce multiple teeth designs and multiple teeth in fewer manufacturing steps.
6. A method of assembling a spherical reamer using multiple panels, pre-stamped with teeth of specific geometry and orientation.

In certain embodiments, the approach to producing more efficient medical reamers described herein can help ensure a proper bone preparation for patients with varying anatomy and/or pathology. In addition, the cutting tools described herein can provide improved sharpness, reduced heat during the reaming and a faster preparation based on tooth geometry and orientation. These improvements are also possible through a less expensive manufacturing process which makes it more economical to discard the reamer when it becomes dull.

Functional Life of Cutting Tools

It is also desirable to understand the effective functional life of the cutting tools described herein. As with any cutting tool, no matter how efficient the cutter has been designed, it will dull after multiple uses and its effective life will have terminated. Currently medical spherical reamers are used multiple times without any monitoring of the status of where the cutter is in its life cycle. Hospitals receive a new spherical reamer and follow an instrument processing procedure that includes cleaning, sterilizing, use, cleaning, sterilizing, and reuse. However, that cycle can continue for many, many surgical procedures before a surgeon notices the reamer is not cutting well.

Cutting teeth dull after even a few uses and dull cutting teeth generating heat that can be sufficient to cause bone necrosis. Accordingly, in addition to improving teeth design, it can also be helpful to provide the ability to indicate when a cutter should be removed from use to avoid issues relating to bone necrosis from dull cutters. In conventional approaches, instruments are used in hospitals on patients many times without knowledge of the life expectancy of the reamer and often beyond the functional life of the instrument. Some of the reluctance to discard the instrument after a single use is the cost of manufacturing these instruments. It is also perceived by the medical industry through orthopedic surgeons that these instruments do have a functional life greater than a single use. Accordingly, significant improvements in manufacturing costs, such as those realized by the embodiments described herein, can help to reduce the number of uses needed to obtain a return on investment.

The methods described herein can create more cost effective cutting tools, such as spherical/hemispherical reamers. In addition, the methods described herein can provide a means for defining the effective functional life of the cutting tools and providing a method of knowing when to discard it to ensure that the cutting tool used for any procedure (e.g., a total hip procedure) will be effective for its intended purpose.

In at least some of the embodiments described herein, as described above, medical reamers can include at least some of the following design parameters, enabling the production of more efficient tools for cutting bone:

1. Optimize forces applied to the reamer.
2. Thin, sharp tooth edge.
3. Specific tooth designs and tooth orientations providing a faster completion of the reaming cycle.
4. Adequate bone chip exit path to minimize friction from the flow of the chips at the cutter surface.
5. Minimize friction from cutting by using thinner materials and improved tooth geometry.
6. Define the functional life of the cutting edges through laboratory testing to know when to discard the reamer.
7. Provide an improved and efficient manufacturing process.

Laboratory testing to confirm an improved speed of the preparation, a lower cutting exposure temperature to the bone and an increased functional life to the reamer.

Additional Embodiments of Hemispherical Cutting Tools

FIGS. 15A-15E illustrate another embodiment of a cutting tool configured as a spherical or hemispherical reamer 100. The hemispherical reamer 100 can comprise a plurality of panels (e.g., stamped panels) coupled to a frame. In the illustrated embodiment, the reamer 100 can comprise a base portion, first end portion, or equatorial portion 102, and a top end portion, second end portion, or pole end portion 104 located at the top of the hemispherical body. In the illustrated embodiment, the reamer 100 can comprise a plurality of curved first panel members referred to herein as side panel members or side panels 106 arrayed circumferentially around the reamer. The reamer 100 can further comprise at least one second panel member referred to herein as a dome panel 108 located at the top or pole of the reamer. The panels 106 and 108 can be secured to a frame 110, which in certain embodiments can be an injection molded polymeric frame. In the illustrated configuration, the hemispherical reamer 100 includes four side panels 106 circumferentially spaced apart by 90°, although the reamer can include any number of side panels 106 at any angular spacing. The hemispherical reamer 100 can be driven about its central axis or axis of rotation 121.

In certain embodiments, the panel members 106 and/or 108 can be metal panels stamped and/or laser cut to a specified shape. In certain embodiments, the panels can be stamped or cut from flat sheet stock, and can undergo one or more additional processing or forming steps to, for example, form cutting edges or cutting teeth, to be formed into a concavo-convex/curved shape, etc. In certain embodiments, the panel members 106/108 can comprise any of various high-strength, bio-compatible metals such as stainless steel, carbon steel, titanium or titanium alloys, tungsten carbide, nickel-titanium alloys, etc.

Figure 16A:
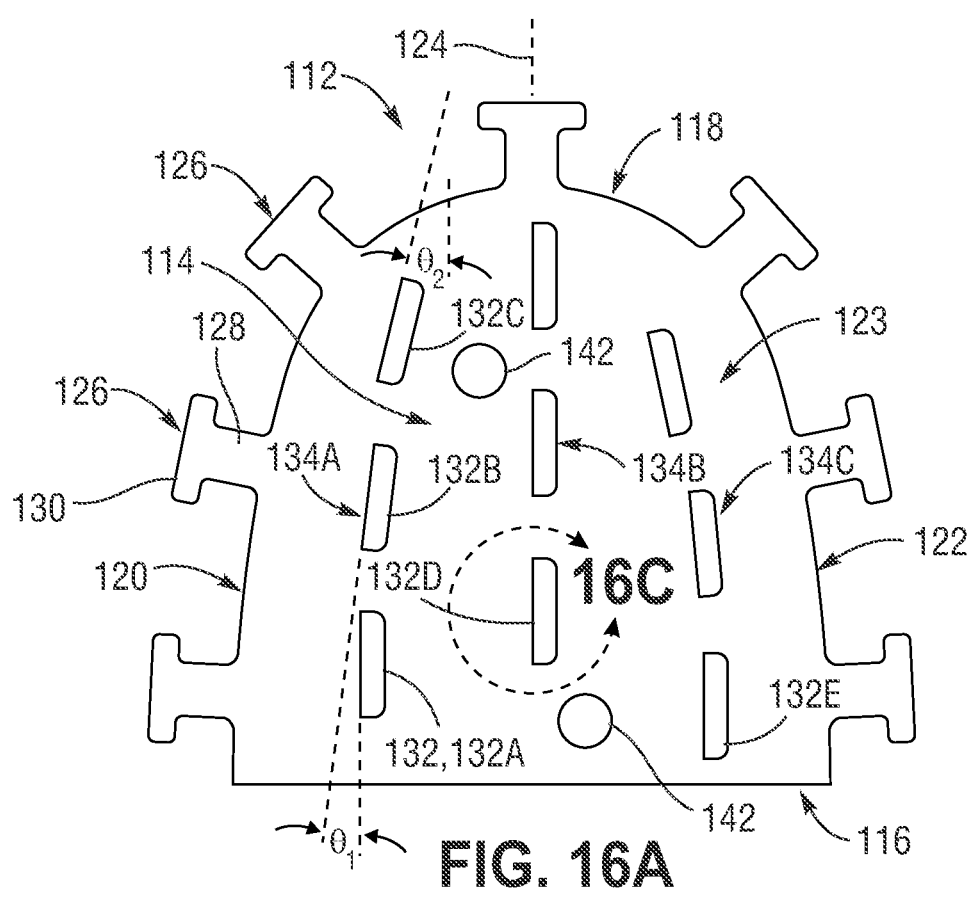
FIGS. 16A and 16B are top and bottom plan views, respectively, of a curved side panel blank.
Figure 16B:
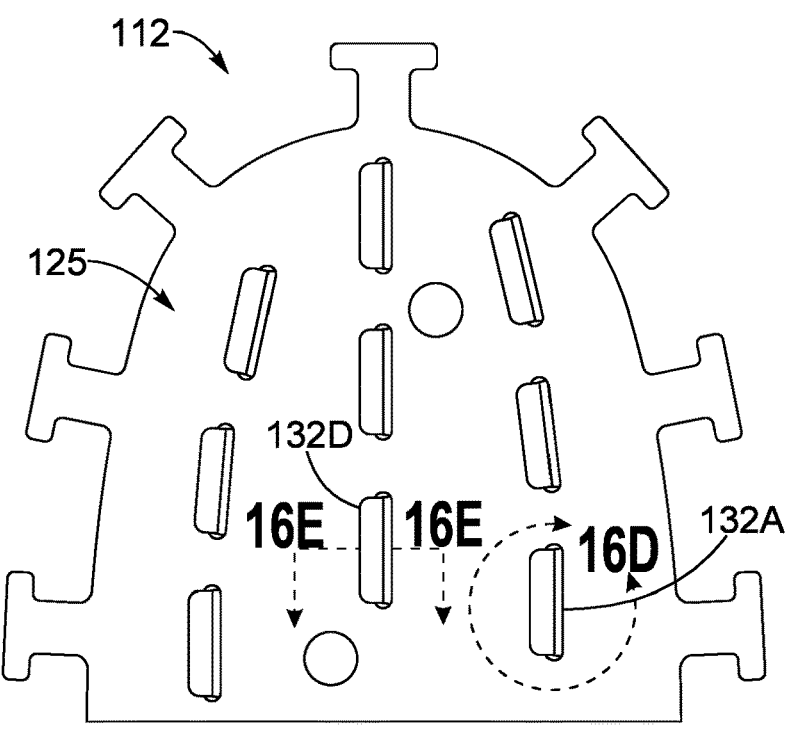

FIGS. 16A-16E illustrate a representative embodiment of a side panel member blank 112 which can be further processed to form a side panel member 106. FIG. 16A illustrates a first or outer surface 123 of the blank 112 configured to be on the exterior of the reamer 100, and FIG. 16B illustrates a second or inner surface 125 of the blank 112 configured to be on the interior of the reamer. The blank 112 can be, for example, stamped or laser cut from flat sheet stock. The blank 112 can comprise a main body portion 114 having a first or proximal end portion 116 with a straight edge portion, and a second or distal end portion 118 with a curved edge portion. Side edge portions 120 and 122 can extend between the first end portion 116 and the second end portion 118, and can curve inwardly generally toward a longitudinal axis 124 of the blank.

Referring to FIG. 16A, the blank 112 can comprise a plurality of engagement members 126 extending from some or all of the edge portions. In the illustrated embodiment, the blank 112 can include engagement members 126 extending from the edge portions 120, 122, and 118, although other combinations are possible. For example, in other embodiments the blank 112 can include engagement members 126 extending from each edge portion including the first edge portion 116, or only the side edge portions 120 and/or 122, or combinations of the first or second end portion 116, 118 and one or both of the side edge portions 120, 122. In the illustrated embodiment, the engagement members 126 are T-shaped members with first members 128 coupled to the main body 114 of the blank, and second members configured as cross members 130 at the ends of the engagement members 126 and forming free ends of the engagement members. In the illustrated embodiment the blank 112 includes seven engagement members 126, although the blank can include any number of engagement members having any shape, spacing, and/or size. In certain embodiments, the engagement members can define openings (e.g., in the members 128) to allow material of the frame 110 to flow through the openings to interlock the panel 106 to the frame. In yet other embodiments, the engagement members 126 can be L-shaped (e.g., with a cross member 130 extending from one side of the first member 128), or can include more than one cross member extending in different planes, such as a second cross member extending into and/or out of the plane of the page in FIG. 16A.

The blank 112 can comprise a plurality of cutting teeth 132 arranged in one or more columns. In the illustrated embodiment, the blank 112 includes three columns 134A, 134B, and 134C of cutting teeth 132. Each of the columns includes three cutting teeth 132, although in other embodiments the blank can include more or fewer columns and/or teeth. In the illustrated embodiment, the central column 134B of cutting teeth is aligned with the axis 124, while one or more of the teeth of the columns 134A and 134C can be angled inwardly toward the axis 124, although the columns 134A and 134C can also be aligned with the axis 124. For example, referring to the column 134A by way of illustration, the lowermost cutting tooth 132A of the column can be aligned or substantially aligned with the axis 124, while the second cutting tooth 132B can be inclined or angled toward the axis 124 by an angle $\theta_1$ relative to a line parallel to the axis 124, and the uppermost tooth 132C can be angled toward the axis 124 by an angle $\theta_2$, which in some embodiments can be greater than the angle $\theta_1$. In certain embodiments, the angle $\theta_1$ and/or the angle $\theta_2$ can be from 1° to 45°, 2° to 30°, 3° to 30°, 1° to 10°, 1° to 20°, 3° to 10°, 3° to 20°, etc.

Figure 16C:
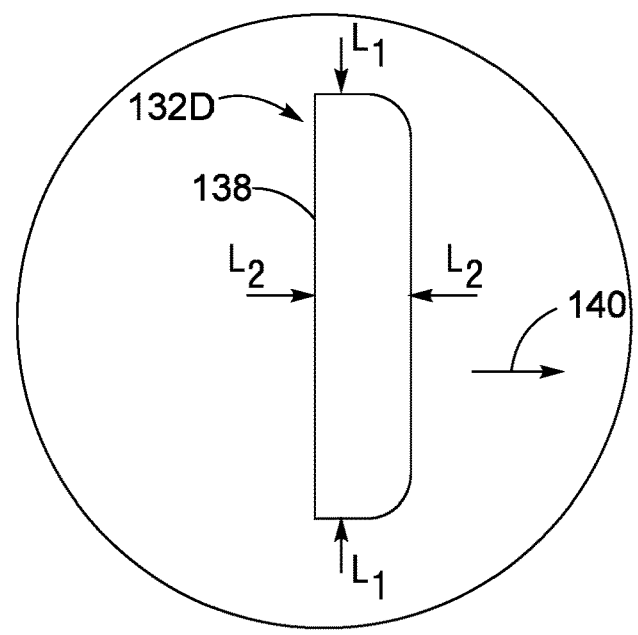
FIGS. 16C and 16D are magnified top and bottom plan views, respectively, of a cutting tooth of the curved side panel blank of FIGS. 16A and 16B.

Referring to FIG. 16C, the cutting teeth 132 can comprise openings/slots defined in the panels and having a first/major/long axial dimension $L_1$ oriented generally along the longitudinal axis 124 (FIG. 16A), and a second/minor/short axial dimension $L_2$ extending generally along an axis perpendicular to the axis 124 in the plane of the page. In certain embodiments, once the blank 112 has been formed into a curved/concavo-convex shape and attached to the cutter, the long axial dimension $L_1$ can extend longitudinally along the hemispherical surface of the cutter (e.g., along lines of longitude between the equatorial portion 102 and the polar end portion 104). With reference to the representative cutting tooth 132D illustrated in FIG. 16C, in the illustrated embodiment the cutting surfaces/edges 138 of the teeth are located on the left-hand aspect of the cutting teeth, and the direction of rotation or cutting direction is to the right as indicated by arrow 140.

In the illustrated embodiment, the major axes of the cutting teeth of the respective columns can be configured such that an arc swept by one tooth overlaps with one or more other teeth in adjacent columns. For example, returning to FIG. 16A the longitudinal position of the cutting tooth 132A along the axis 124 at least partially overlaps with the longitudinal position of cutting tooth 132D in column 134B which, in turn, at least partially overlaps with the cutting tooth 132E of column 134C. The cutting edges of cutting teeth of adjacent or sequential columns (e.g., in the direction of rotation) are thus longitudinally offset from each other along the surface of the reamer. The cutting teeth 132A and 132E also partially overlap in the circumferential direction. In this manner, the various cutting teeth of the reamer sweep an area that is coextensive with the surface area of the reamer (e.g., there are few if any locations on the surface of the reamer where incident bone will not be cut by the cutting teeth). In certain embodiments, the cutting tooth configurations can lend themselves to manufacture by stamping, and can advantageously create an opening to allow bone debris to flow into the body of the reamer during cutting. For example, in certain embodiments the opening of the cutting teeth can be stamped or punched in a first step, and the edge intended to form the cutting edge (e.g., edge portion 138 in FIG. 16C) can be upset or uplifted in a second stamping step that does not punch or extend through the panel. In certain embodiments, the cutting edge can also be simultaneously pressed/compressed during the uplifting step. This can stamp/compress/extrude the material, thereby reducing its thickness to form a sharp cutting edge. For example, in a representative embodiment the material thickness prior to the edge formation stamping step can be 0.012 inch (0.30 mm), and the resulting edge after stamping can have a thickness of 0.003 inch (0.076 mm), yielding a thin, sharp cutting edge.

In the illustrated embodiment, the blank 112 can also include one or a plurality of round openings 142 (FIG. 16A) defined in the main body. In certain embodiments, openings 142 can function as datum holes/openings to facilitate accurate positioning of the panels in the injection molding tool when forming the frame as described below.

Figure 16D:
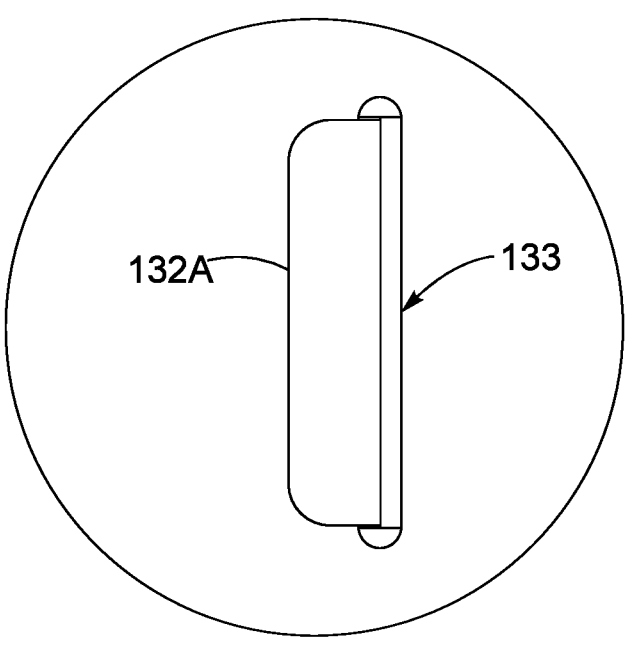

FIG. 16D is a magnified view of the inner surface of the representative cutting tooth 132A. The region 133 indicates the portion of the panel which can be uplifted during the second stamping step described above.

Figure 16E:
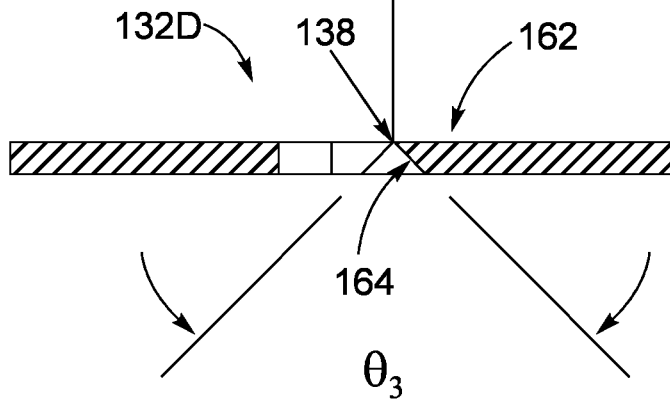
FIG. 16E is a cross-sectional view of a cutting tooth taken along line 16E-16E of FIG. 16B.

FIG. 16E is a magnified cross-sectional view taken along line 16E-16E in FIG. 16B. The cutting tooth 132D can comprise an external surface 162 and an angled internal surface 164 which can meet or coincide at an edge portion 138. In certain embodiments, the edge portion 138 can form the cutting edge of the tooth, as discussed in greater detail with reference to FIG. 22B below. In certain embodiments, the internal surface 164 can define an angle $\theta_3$ (e.g., measured relative to the surface of the panel). In certain embodiments, the angle $\theta_3$ can be 60° to 120°, 80° to 100°, or 90° in particular embodiments.

Figure 17:
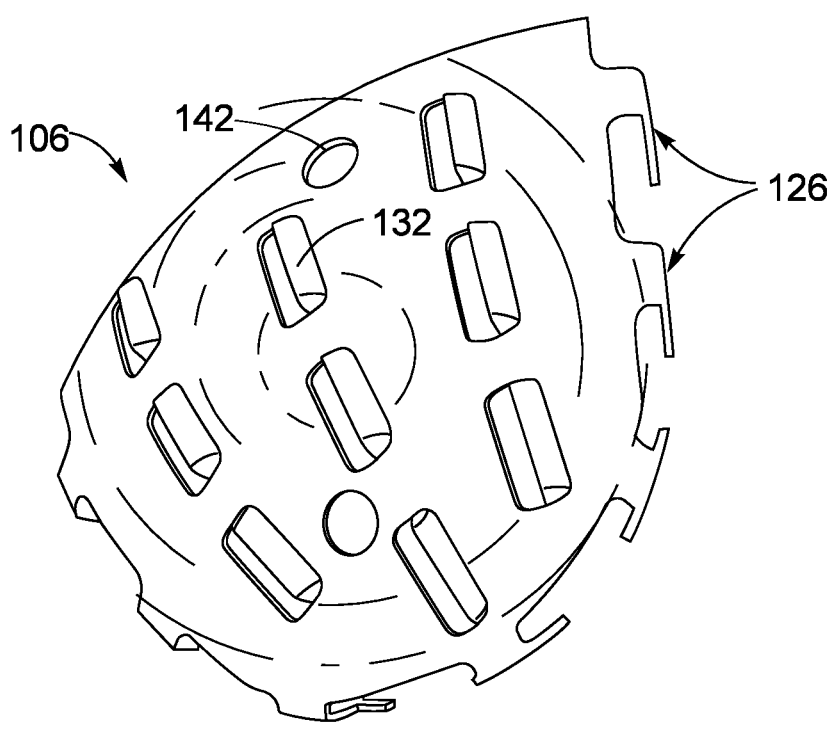
FIGS. 17 and 18 are perspective views of a curved side panel, according to one embodiment.
Figure 18:
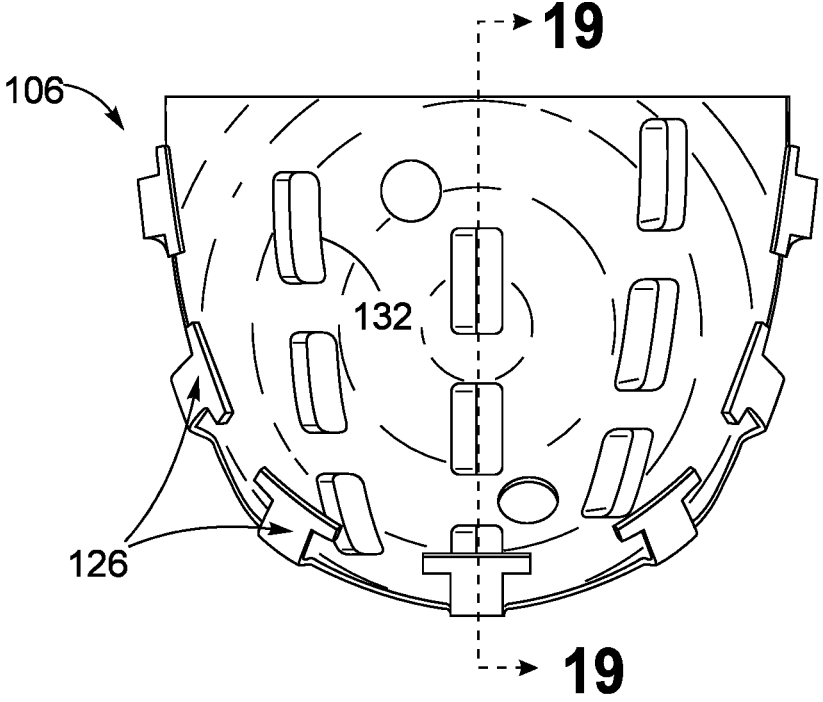
Figure 19:
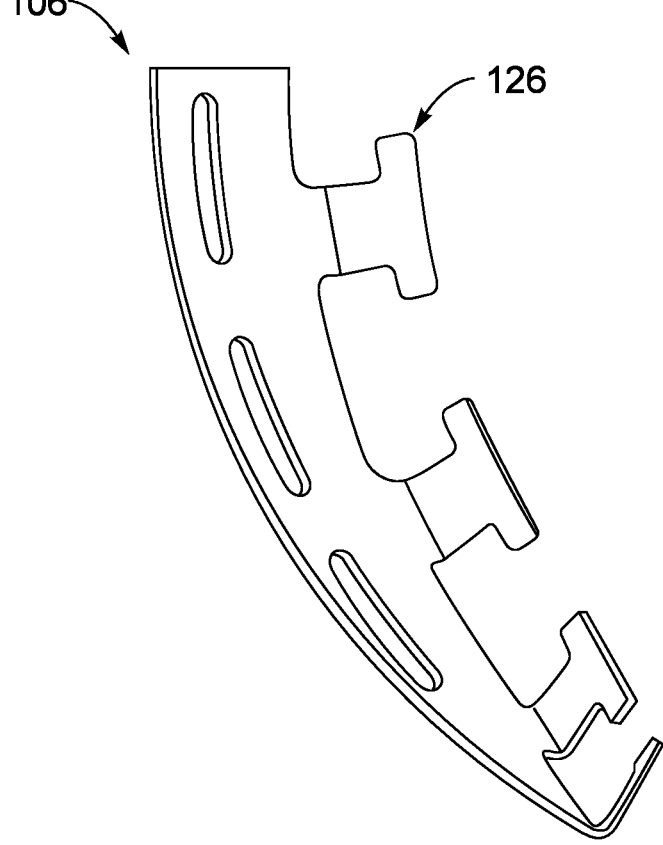
FIG. 19 is a cross-sectional view of a curved side panel taken along line 19-19 of FIG. 18.

FIGS. 17-19 illustrate the blank 112 after it has been formed into a curved side panel 106. In certain embodiments, the main body 114 can be formed/bent/pressed into a curved shape, and the engagement members 126 can be bent or curved such that they extend radially inward (e.g., toward the interior of the body of the hemispherical reamer and/or toward the central axis 121 of the hemispherical reamer). In certain embodiments, the engagement members 126 can be formed by stamping, and can be bent toward the interior of the reamer body in a separate stamping step, or together with one of the stamping steps above (e.g., formation of the cutting teeth).

Figure 20A:
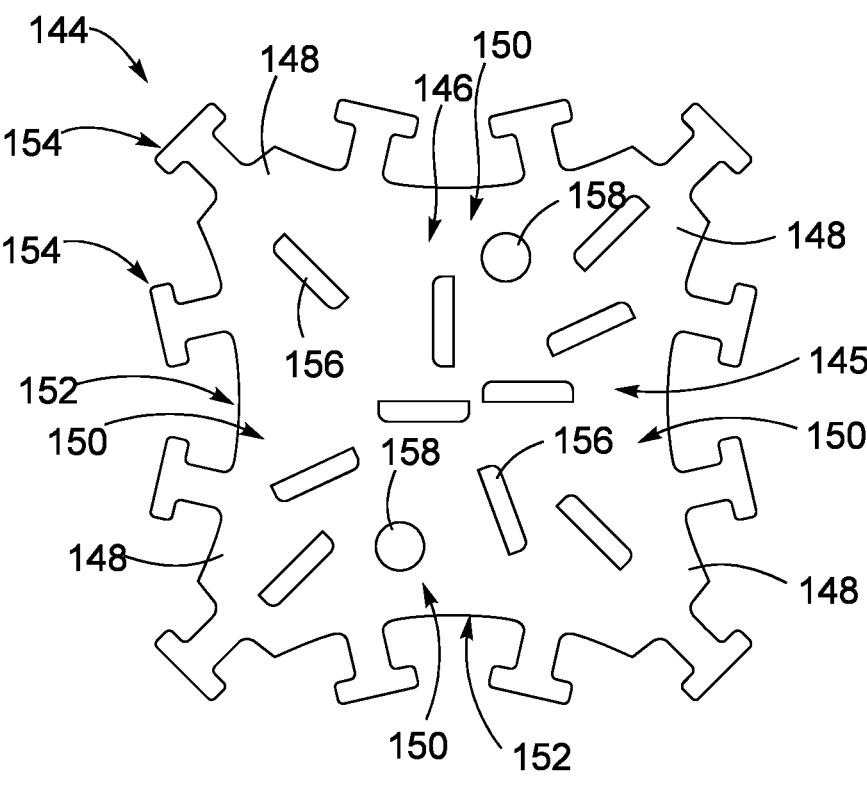
FIGS. 20A and 20B are top and bottom plan views, respectively, of a top panel blank, according to one embodiment.
Figure 20B:
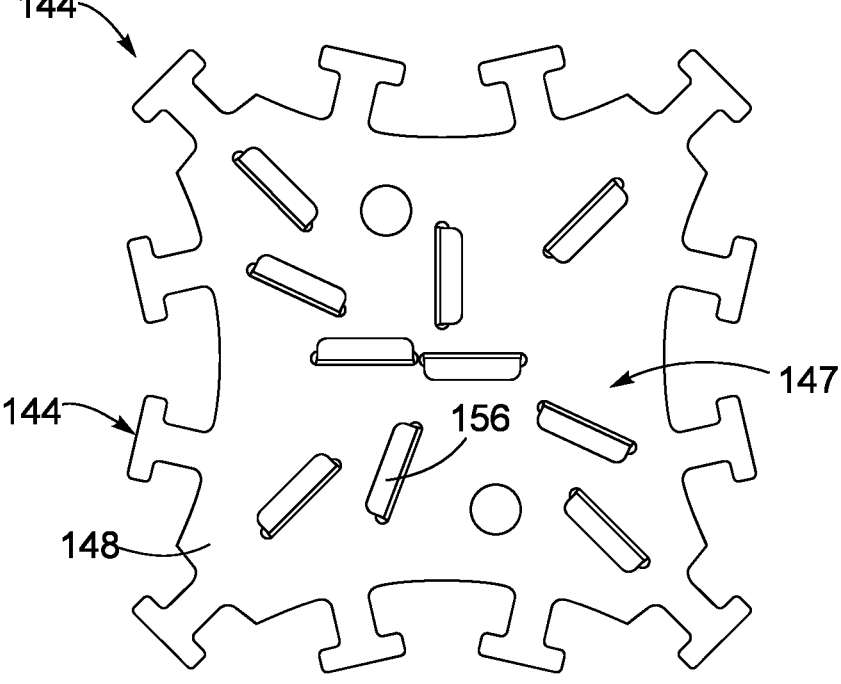

FIGS. 20A and 20B illustrate a representative example of a dome panel member blank 144, according to one embodiment. FIG. 20A illustrates the outer surface 145 of the blank, and FIG. 20B illustrates the inner or interior surface 147 of the blank. The dome panel blank 144 can comprise a main body portion 146 and a plurality of extension portions, apices, or lobes 148 around its perimeter. For example, in the illustrated embodiment the blank 144 includes four lobes 148, with each lobe defining a corner of a generally rectangular or square outline of the main body portion 146. Curved edge portions 150 can extend between the lobes 148. The curved edge portions 150 can comprise concave or inwardly recessed/curved edges 152 at least partially defining the perimeter of the blank 144 between the lobes 148.

The blank 144 can comprise a plurality of engagement members 154 extending outwardly from the edge portions of the blank. For example, in the illustrated embodiment each curved edge portion 150 includes two engagement members 154, and each lobe 148 includes an engagement member axially aligned with the lobe 148, although the blank may include more or fewer engagement members arranged in any arrangement. In the illustrated embodiment, the engagement members 154 are configured as T-shaped members similar to the engagement members 126 of FIG. 16A, but may have different configurations.

The blank 144 can further comprise a plurality of cutting teeth 156. In the illustrated embodiment, the blank 144 can comprise a cutting tooth 156 axially aligned with each lobe 148 (e.g., wherein an edge of the cutting tooth structure is aligned with the longitudinal axis bisecting the lobe 148). The blank 144 can also include one or a plurality of circular openings 158 defined in the panel member, which can be configured as datum openings as described above.

FIGS. 21A-21C illustrate the blank 144 after it has been formed into the dome panel 108. The main body portion 146 can be curved or concave according to the curvature of the hemispherical reamer 100. The engagement members 154 can be bent/folded/curved such that they extend from the main body portion 146 at an angle generally in a direction away from the apex 160 (FIG. 21C) of the outer surface 145 on the concave side of the panel. With reference to FIG. 21C, in certain embodiments the engagement members 154 of axially aligned lobes 148 (e.g., lobes on opposite sides of the main body portion from each other) can define an angle $\alpha$. In certain embodiments, the angle $\alpha$ can be 1° to 30°, 1° to 20°, or 5° to 15°. In particular embodiments, the angle $\alpha$ can be 10°. In certain embodiments, the engagement members 154 of the dome panel 108 can be arranged such that in the assembled reamer, the engagement members 154 of the dome panel 108 are arranged alternatingly with the engagement members 126 of the curved side panels 106 at least where the curved distal end portions 118 of the side panels 106 are received by the corresponding curved edges 152 of the dome panel (FIG. 15B).

In certain embodiments, the dome panel 108 can comprise a central or longitudinal axis 157 illustrated in FIG. 21C, and indicated by the intersection of dashed lines 159 and 161 in FIG. 21B. In certain embodiments, the axis 157 can be aligned with the axis 121 of the reamer after assembly. In the illustrated embodiment the dome panel 108 can comprise a first or innermost cutting tooth 156A having a cutting edge 163 that is located on, coincident with, or intersects the longitudinal axis 157 (e.g., in FIG. 21B the longitudinal axis 157 extends into the plane of the page tangent to the cutting edge 163). In the illustrated embodiment, longitudinal axis 157 can divide the cutting edge 163 into a first portion 165 and a second portion 167. The first portion 165 can be larger than the second portion 167 such that the center of the cutting edge 163 is offset radially outwardly from the longitudinal axis 157 toward the edge of the dome panel. Because the cutting edge 163 extends across the longitudinal axis 157, the cutting edge sweeps around and/or across the longitudinal axis 157 when the reamer is rotated. Additionally, the path/arc swept by the cutting teeth 156B and 156C can at least partially overlap with the path/arc swept by the cutting tooth 156A. In this manner, the teeth of the dome panel 108 can be staggered, overlapping, and/or configured to avoid creating a positive burr of bone at the north pole of the reamer. The paths of the cutting teeth 156B and 156C, in turn, can overlap with the paths of the cutting teeth 156D, 156E, and 156F, and so on to the outermost cutting teeth.

FIGS. 22A and 22B illustrate a representative embodiment of a cutting tooth 156 (or 132) after formation of the cutting edges 138. As noted above with reference to FIG. 16E, the cutting teeth can comprise a first or outer surface 162 and a second or inner surface 164 that meet at the cutting edge 138. The surface 162 and the surface 164 can define an angle $\omega_1$. In certain embodiments, the angle $\omega_1$ can be 30° to 70°, 40° to 60°, or 45°. The outer surface 162 can also define an angle $\omega_2$ with an axis 166 tangent to the cutting edge 138 at the apex of the surfaces 162 and 164. In certain embodiments, the angle $\omega_2$ can be 10° to 60°, 15° to 45°, 20° to 30°, or 25°. The cutting surfaces 138 can also have a tooth height H, which can be 0.25 mm to 1 mm, such as 0.5 mm, or any of the tooth heights described herein.

FIG. 23 illustrates a representative embodiment of the frame 110. In certain embodiments, the frame 110 can comprise a first/lower/base member or portion 168, and a second/upper/top member or portion 170. The second frame member 170 can comprise a plurality of angularly spaced, curved extension members 172 configured to engage the first member 168.

For example, FIGS. 24A and 24B illustrate top and bottom plan views, respectively, of the first member 168. Referring to FIG. 24A, the first member 168 can comprise an outer annular body, portion, and/or ring portion referred to hereinafter as a ring member 174. The first member 168 can further comprise four cross members 175, 176, 177, and 178 extending across the inner diameter of the ring member 174 and joined at the center of the ring member. Any or all of the ring member 174 and/or the cross members 176-178 can comprise a round or curved cross-section (e.g., as shown in FIG. 25).

The upper/distal aspect or surface of the first member 168 can comprise a plurality of coupling portions generally indicated at 180 (FIG. 24A) arranged circumferentially around the member 174. As best shown in FIG. 24A, in the illustrated embodiment the coupling portions 180 can be curved in the circumferential direction, although the coupling portions can also be straight. With reference to FIG. 25, each of the coupling portions 180 can comprise a recessed portion or surface 182 offset inwardly toward the central axis of the ring member 174 (e.g., in the proximal direction when the reamer is oriented for use). The coupling portions 180 can further comprise a first extension portion or projection 184 extending outwardly from the surface 182, and a second extension portion or projection 186 extending outwardly from the first projection 184. In the illustrated embodiment, the cross-sectional shape of the first projection 184 can be generally rectangular, and can comprise tapered or chamfered edges. The cross-sectional shape of the second projection 186 can be triangular, although the second portion can also be rectangular, round, etc. In certain embodiments, one or both of the first projections 184 and/or the second projections 186 can be curved (FIG. 24A), and can have a radius proportional to the radius of the equatorial portion 102 of the hemispherical reamer. In certain embodiments, one or both of the first projections 184 and/or the second projections 186 can be curved along an arc of a circle. Referring again to FIG. 25, in certain embodiments the surfaces of the triangular projections 186 can define an angle $\beta$ of, for example, 20° to 70°, 30° to 60°, 40° to 50°, or 48°.

In the illustrated embodiment, the first member 168 comprises four coupling portions 180 and corresponding projections 184 and 186, but can include any number of coupling portions and/or projections. In other embodiments, one or more of the coupling portions 180 can comprise projections while one or more of the coupling portions comprise openings, recesses, or other coupling structures.

FIGS. 26-28 illustrate the second frame member 170 in greater detail. The second frame member 170 can comprise a first end portion generally indicated at 188 and a second end portion generally indicated at 190. The second end portion 190 can comprise an annular portion or collar portion 192. The extension members 172 can extend from the collar portion 192 and can curve outwardly relative to a central axis 194 (FIG. 23) of the second end portion 190. The extension members 172 can be curved in the longitudinal direction such that they converge toward the second end portion 190. The extension members 172 can also be curved or rounded in the circumferential direction relative to the axis 194 according to the hemispherical shape of the assembled reamer such that the panel members and extension members cooperate to form the outer surface of the hemispherical reamer. Referring to FIG. 26, the first end portion 188 can be at least partially defined by free end portions 196 of the members 172, and can have a diameter that is greater than the diameter of the annular portion 192.

Referring again to FIG. 26, the free end portions 196 of the extension members 172 can comprise curved openings/recesses/channels 198 extending generally in the circumferential direction and configured to receive the coupling portions 180 (e.g., the projections 184 and/or 186) of the first frame member 168. In other embodiments, the first frame member 168 can comprise openings similar to the openings 198 and the second frame member 170 can comprise coupling portions including one or more extensions or projections.

Referring to FIG. 27, the collar portion 192 can have a generally quadrilateral, rectangular, or square perimeter or outline. The collar portion 192 can comprise radiused or curved recessed portions 103 at each corner of the collar portion. Straight edge portions 105 can extend between the recessed portions 103. In certain embodiments, the second frame member 170 can provide structural support for the spherical reamer. The second frame member 170 can have a thickness sufficient to encapsulate the T-shaped engagement members 154 of the various panels. For example, the extension members 172 can be sufficiently thick in the radial direction that the engagement members 154 of the panel members can be embedded in the extension members. The extension members 172 can also be of sufficient strength and thickness to allow assembly of the first frame member/back plate 168 onto the frame member 170, and to resist deformation as the reamer is driven with a driver/power tool coupled to the first frame member 168.

FIG. 28 is a cross-sectional view of the second frame member 170 taken along line 28-28 of FIG. 27. In the illustrated embodiment, the second frame member 170 comprises four extension members 172, but in other embodiments the frame member can include more or fewer extension members, such as three extension members (FIG. 32), five extension members, six extension members, etc.

In a representative example, the various panels 106 and 108 can be stamped, cut (e.g., laser cut), milled, punched, etched (e.g., as part of a lithography process) etc., from metal sheet stock, and the various cutting teeth, openings, and/or engagement members can be formed according to any of the methods described herein. The various panels 106 and/or 108 can then be formed to the appropriate curvature. In certain embodiments, the flat panels can be curved through a series of dies which progressively bend the panels to the specified panel contour. In certain embodiments, such bending can be done in a series of steps to avoid abrupt changes in geometry, which can result in cracks in the panel material. In certain embodiments, after the panel has been formed to the specified contour/radius, the T-shaped engagement members 126/154 can be bent inwardly, for example, in a stamping operation.

The panels 106 and 108 can then be situated in a form/mold/fixture, and some or all of the frame member 110 can be injection molded around the panels such that at least a portion of the outer surfaces of the panels are exposed, and such that at least the engagement members 126/154 are embedded in the frame member 110. For example, in certain embodiments one or both of the frame members 168 and/or 170 can be injection molded around the panels 106, 108. In certain embodiments, the frame member 170 can be injection molded around the panel members, and the frame member 168 can be separately formed and attached to the frame member 170 and/or to the lower edges of the side panels 106 (e.g., by heat bonding, sonic welding such as ultrasonic welding, adhesive, fasteners, or any other fastening or securing means). In certain examples, adhesive can be applied to the coupling portions 180 of the first frame member 168 and/or to the openings 198 after formation of the second frame member 170. In certain embodiments, the male coupling portions 180 of the first frame member 168 can be mated with/received in the female openings 198 in the extension members 172 of the second frame member 170, and the frame members 168 and 170 can be ultrasonically welded together at the junctions. In certain embodiments, the frame members 168 and 178 can both be injection molded around the panels (e.g., in the same molding operation). In certain embodiments, the frame can be a unitary body in which the first frame portion and the second frame portion are integrally formed.

In a representative embodiment, the frame member 170 can be formed in an injection molding tool, such as in a representative mold 200 illustrated in FIG. 29. The mold 200 can comprise two separable portions or halves 202 and 204 which, when coupled together, can define a cavity shaped to produce the frame member 170. The portion 202 can define a recess 206 comprising a plurality of smaller recesses or indentations 208 configured to accommodate the cutting teeth of the panels 106/108. The portion 204 can comprise a projection/extension portion 210 comprising grooves 212 corresponding to the extension members 172 of the frame member 170.

To produce the frame member 170, a plurality of stamped panels 106 and 108 can be positioned within the mold (e.g., in or on the mold portion 202 and/or 204). The portions 202 and 204 can then be assembled/secured together such that the projection portion 210 of the member 204 is received in the recess 206 of the member 202, and material (e.g., a polymeric material/plastic material) can be injected into the cavity to create the second frame member 170 with incorporated panels 106/108. The polymeric material can include any suitable injection-moldable, medical grade plastic (e.g., PEI (polyetherimide, ULTEM®), PEEK (polyetheretherketone), PAI (polyamidide, TORLON®)). The frame member 168 can be formed in a similar manner by injection molding, and can be secured to the frame member 170 with the incorporated panels as described above to create the reamer 100.

The hemispherical reamer 100 can provide a number of significant advantages. For example, the hemispherical reamer 100 can be quickly and economically produced, and can provide the cut accuracy and low temperature/low friction operation of significantly more expensive reamers. This can allow hemispherical reamers according to the embodiments described herein to be more economically discarded at the end of their useful lives, reducing the risk of heat-related necrosis from dull cutters, the risk of surgical site infection, and the expense of cleaning and sterilizing cutters for repeated use on multiple patients.

FIGS. 30 and 31 illustrate another embodiment of the hemispherical cutting tool 100 in which the dome panel 108 has cutting teeth 179A and 179B (FIG. 30) with corresponding openings that are interconnected by a slot 181 extending over the pole of the dome panel and separating the oppositely oriented cutting edges of the teeth 179A and 179B. Referring to FIG. 31, the second frame member 170 can comprise walls 183 extending distally from the second end portion 190 between extension members 172.

FIG. 32 illustrates another embodiment of a hemispherical cutting tool 300. The hemispherical cutting tool 300 can comprise a first or distal frame member 302 (e.g., an injection molded frame member) having a central annular portion 304 and a plurality (e.g., three) of extension portions or members 306 extending radially outwardly from the annular portion 304. The extension members 306 can be coupled to a second or proximal frame member 308. A plurality of curved side panels 310 having two rows of cutting teeth 312 can be coupled to the second frame member 308, for example, by injection molding the second frame member around the side panels and a dome panel 314 as described above. In certain embodiments, the side panels 310 and the dome panel 314 of the cutting tool 300 can comprise engagement members similar to the engagement members 126/154 described above. In certain embodiments, the first frame member 302 can be coupled to the second frame member 308 by ultrasonic welding, or by any other coupling structure/method. In certain embodiments, the frame can be a unitary body in which the frame member 302 and the frame member 308 are formed in the same molding operation.

In certain embodiments, the first frame member 302 can provide a plurality of options for coupling (e.g., quick-connect coupling) to a drive shaft (e.g., a reamer shaft). In certain embodiments, the interior volume of the cutting tool 300 can be configured to accommodate a specified volume of reamed bone/bone shavings/cuttings according to the particular procedure to be performed. In certain embodiments, the first and/or second frame members can be color coded to indicate a specified size of the cutting tool.

FIG. 33 illustrates an exploded view of the hemispherical cutting tool 300. In the illustrated embodiment, the side panels 310 can comprise a respective lobe 320 at the upper or distal end of the side panels (e.g., relative to a use orientation of the cutting tool). The lobes 320 can extend from the main body of the side panels 310 in the direction of the pole of the cutting tool. In certain embodiments, the lobes 320 can be wholly offset to one side of a longitudinal axis 322 of the side panels 310. In certain embodiments, the longitudinal axis 322 can pass through openings 324 (e.g., datum openings) of the side panels. The lobes 320 can include cutting teeth 312 (FIG. 32). Thus, the row of cutting teeth 312 aligned with the lobe 320 can include an additional cutting tooth relative to the other row of cutting teeth on each panel.

The dome panel 314 can also comprise a plurality of circumferentially spaced apart lobes 326 extending outwardly from a round or circular main body of the dome panel 314. A plurality of the lobes 326, such as all of the lobes 326 or a subset of the lobes, can comprise cutting teeth 312. When the side panels 310 and the dome panel 314 are coupled to the frame 302/308, the side panels 310 be oriented such that lobes 320 of the side panels are received between lobes 326 of the dome panel 314 (e.g., the lobes 320 of the side panels alternate with the lobes 326 of the dome panel in the circumferential direction). Two side panels, such as side panels 310A and 310B in FIG. 33 can be arranged with their lobes 320 adjacent each other, and those two lobes 320 can be received between a pair of lobes 326 of the dome panel 314. The cutting teeth 312 of the panels 310A and 310B can also be oriented in opposite circumferential directions.

The frame 302/308 can comprise a plurality of openings or windows 328 defined by circumferentially spaced apart, longitudinally extending frame members 330. The openings 328 can be covered by respective side panels 310. The frame 302/308 can also comprise a polar opening 332, which can be covered by the dome panel 314 in the assembled state.

Any of the features/configurations of the cutting tool 100 and/or the cutting tool 300 can be used or applicable in combination with any of the cutting tool embodiments described herein. In certain embodiments, any of the cutting tool embodiments described herein can be packaged together with any of a variety of other accessories including drive shafts, guides, etc., in a sterile kit or surgical pack.

In view of the many possible embodiments to which the principles of the disclosure may be applied, it should be recognized that the illustrated embodiments are only examples and should not be taken as limiting the scope of the claimed subject matter. Rather, the scope of the claimed subject matter is at least as broad as the following claims and their equivalents.

The invention claimed is:

1. A hemispherical cutting tool, comprising:
   a frame having a first end portion and a second end portion, and defining an axis of rotation of the hemispherical cutting tool;
   a plurality of curved side panels coupled to the frame and arranged about the axis of rotation of the cutting tool, the curved side panels comprising a plurality of cutting teeth and a plurality of engagement members extending inwardly into the frame from edge portions of the curved side panels and bent in a direction toward a hollow interior of the hemispherical cutting tool; and
   a dome panel coupled to the second end portion of the frame such that the cutting tool has a hemispherical shape, the dome panel comprising a plurality of cutting teeth and a plurality of engagement members extending inwardly from edge portions of the dome panel into the frame and bent in a direction toward the hollow interior of the hemispherical cutting tool;
   wherein the frame is injection molded around the curved side panels and the dome panel such that the engagement members of the curved side panels and the dome panel are embedded in the injection molded frame.

2. The hemispherical cutting tool of claim 1, wherein side edge portions and distal edge portions of the curved side panels comprise engagement members.

3. The hemispherical cutting tool of claim 1, wherein the engagement members of the curved side panels comprise T-shaped members.

4. The hemispherical cutting tool of claim 1, wherein the frame comprises a first polymeric frame member comprising an annular body, and a second polymeric frame member comprising a plurality of curved extension members coupled to the annular body of the first polymeric frame member.

5. The hemispherical cutting tool of claim 4, wherein one of the first or second polymeric frame members comprises a plurality of coupling portions configured to be received in openings defined in the other of the first or second polymeric frame members.

6. The hemispherical cutting tool of claim 1, wherein:
   the cutting teeth of the curved side panels are arranged in columns; and cutting edges of the cutting teeth are longitudinally offset from each other in adjacent columns and at least partially overlap with each other in the circumferential direction.

7. The hemispherical cutting tool of claim 1, wherein:
the cutting teeth of the curved side panels are arranged in columns;
the cutting teeth of a central column of cutting teeth of each curved side panel are aligned with a central axis of the curved side panel; and
cutting teeth of columns of cutting teeth that are circumferentially offset from the central column of cutting teeth are angled toward the central column of cutting teeth.

8. The hemispherical cutting tool of claim 1, wherein:
the cutting teeth of the curved side panels comprise a long dimension and a short dimension; and
the long dimensions of the cutting teeth are oriented longitudinally on a hemispherical surface of the cutting tool.

9. The hemispherical cutting tool of claim 1, wherein the axis of rotation of the hemispherical cutting tool intersects a cutting tooth of the plurality of cutting teeth of the dome panel.

10. The hemispherical cutting tool of claim 1, wherein the dome panel comprises a plurality of lobes separated by concave edge portions, each of the lobes comprising an engagement member.

11. A method of making the hemispherical cutting tool of claim 1, comprising:
situating the dome panel and the plurality of curved side panels in a mold; and
injecting a polymeric material into the mold to form at least a portion of the frame.

12. A method, comprising cutting bone with the hemispherical cutting tool of claim 1.

13. The hemispherical cutting tool of claim 1, wherein the engagement members of the curved side panels extend radially inwardly into the frame toward the hollow interior of the hemispherical cutting tool.

14. A hemispherical cutting tool, comprising:
a polymeric frame comprising a first polymeric frame member coupled to a second polymeric frame member and defining an axis of rotation of the hemispherical cutting tool, the first polymeric frame member comprising an annular body and defining a first end portion of the frame, the second polymeric frame member comprising a plurality of curved extension members coupled to the annular body of the first polymeric frame member and converging toward a second end portion of the polymeric frame;
a metal dome panel coupled to the second polymeric frame member at the second end portion of the polymeric frame, the metal dome panel comprising a plurality of cutting teeth; and
a plurality of curved metal side panels coupled to the polymeric frame and arranged about the axis of rotation of the hemispherical cutting tool.

15. The hemispherical cutting tool of claim 14, wherein the curved metal side panels comprise a plurality of engagement members extending inwardly from edge portions of the curved metal side panels into the second polymeric frame member in a direction toward a hollow interior of the hemispherical cutting tool.

16. The hemispherical cutting tool of claim 15, wherein side edge portions and distal edge portions of the curved metal side panels comprise engagement members.

17. The hemispherical cutting tool of claim 15, wherein the metal dome panel comprises a plurality of engagement members extending from edge portions of the metal dome panel inwardly into the second polymeric frame member in a direction toward the hollow interior of the hemispherical cutting tool.

18. The hemispherical cutting tool of claim 15, wherein the engagement members of the curved metal side panels comprise T-shaped members.

19. The hemispherical cutting tool of claim 15, wherein the frame is injection molded around the curved metal side panels and the metal dome panel such that the engagement members of the curved metal side panels and the metal dome panel are embedded in the injection molded frame.

20. The hemispherical cutting tool of claim 14, wherein one of the first or second polymeric frame members comprises a plurality of coupling portions configured to be received in openings defined in the other of the first or second polymeric frame members.

21. The hemispherical cutting tool of claim 14, wherein:
the cutting teeth of the curved metal side panels comprise a long dimension and a short dimension; and
the long dimensions of the cutting teeth are oriented longitudinally on a hemispherical surface of the cutting tool.

22. The hemispherical cutting tool of claim 14, wherein the axis of rotation of the hemispherical cutting tool intersects a cutting tooth of the plurality of cutting teeth of the metal dome panel.

23. The hemispherical cutting tool of claim 14, wherein the metal dome panel comprises a plurality of lobes separated by concave edge portions, each of the lobes comprising an engagement member.

24. A hemispherical cutting tool, comprising:
a frame comprising a first polymeric frame member coupled to a second polymeric frame member and defining an axis of rotation of the hemispherical cutting tool, the first polymeric frame member comprising an annular body and defining a first end portion of the frame, the second polymeric frame member comprising a plurality of curved extension members coupled to the annular body of the first polymeric frame member and converging toward a second end portion of the polymeric frame;
a plurality of curved side panels coupled to the frame and arranged about the axis of rotation of the cutting tool, the curved side panels comprising a plurality of cutting teeth and a plurality of engagement members extending inwardly into the frame from edge portions of the curved side panels in a direction toward a hollow interior of the hemispherical cutting tool; and
a dome panel coupled to the second end portion of the frame such that the cutting tool has a hemispherical shape, the dome panel comprising a plurality of cutting teeth and a plurality of engagement members extending inwardly from edge portions of the dome panel into the frame in a direction toward the hollow interior of the hemispherical cutting tool;
wherein the second polymeric frame member is injection molded around the curved side panels and the dome panel such that the engagement members of the curved side panels and the dome panel are embedded in the second polymeric frame member.

* * * * *